(12) United States Patent
Chen et al.

(10) Patent No.: US 10,398,357 B2
(45) Date of Patent: Sep. 3, 2019

(54) SMART BED SYSTEMS AND METHODS OF OPERATION THEREOF

(71) Applicants: BEDDING WORLD CO., LTD., Taipei (TW); HUIJIA HEALTH LIFE TECHNOLOGY CO., LTD., Zhubei, Hsinchu County (TW)

(72) Inventors: Ying-Chieh Chen, Taipei (TW); Shu-Chen Yang, Zhudong Township, Hsinchu County (TW); Chih-Huan Liu, Taoyuan (TW); Ta-Hsiang Chen, Zhubei (TW); Hsing-Hung Chen, Hukou Township, Hsinchu County (TW)

(73) Assignees: BEDDING WORLD CO., LTD., Taipei (TW); HUIJIA HEALTH LIFE TECHNOLOGY CO., LTD., Zhubei, Hsinchu County (TW)

( * ) Notice: Subject to any disclaimer, the term of this patent is extended or adjusted under 35 U.S.C. 154(b) by 0 days.

(21) Appl. No.: 15/701,356

(22) Filed: Sep. 11, 2017

(65) Prior Publication Data

US 2018/0168485 A1 Jun. 21, 2018

(30) Foreign Application Priority Data

Dec. 16, 2016 (TW) .............................. 105141892 A

(51) Int. Cl.
*A61B 5/11* (2006.01)
*A61B 5/00* (2006.01)
(Continued)

(52) U.S. Cl.
CPC ............ *A61B 5/1115* (2013.01); *A61B 5/002* (2013.01); *A61B 5/0051* (2013.01); *A61B 5/024* (2013.01); *A61B 5/02108* (2013.01); *A61B 5/0816* (2013.01); *A61B 5/1113* (2013.01); *A61B 5/1118* (2013.01); *A61B 5/4809* (2013.01); *A61B 5/4812* (2013.01); *A61B 5/4815* (2013.01); *A61B 5/6887* (2013.01); *A61B 5/6891* (2013.01); *A61B 5/6892* (2013.01);
(Continued)

(58) Field of Classification Search
CPC ........... G08B 21/06; G08B 6/00; G08B 23/00
USPC ....................................................... 340/575
See application file for complete search history.

(56) References Cited

U.S. PATENT DOCUMENTS 9,968,756 B2 * 5/2018 Tsai ..................... A61M 21/02
2005/0190065 A1 9/2005 Ronnholm
(Continued)

FOREIGN PATENT DOCUMENTS

CN 202751551 U 2/2013
CN 103157166 A 6/2013
(Continued)

*Primary Examiner* — Joseph H Feild
*Assistant Examiner* — Sharmin Akhter
(74) *Attorney, Agent, or Firm* — Cheng-Ju Chiang

(57) ABSTRACT

The present invention provides smart bed systems and the operating methods of the smart bed systems. The smart bed systems detect physiological data and sleeping quality with optical fibers which with strong resistance to electromagnetic interference. The smart bed systems do not require the users to wear any wearable devices. The smart bed systems also provide several functions, such as automatic night light, vibration-based alarm, anti-snoring assistance, and scenario-based appliance controls.

16 Claims, 34 Drawing Sheets

(51) Int. Cl.
*G08B 21/22* (2006.01)
*A61B 5/024* (2006.01)
*A61B 5/021* (2006.01)
*A61B 5/08* (2006.01)
*G08B 21/04* (2006.01)

(52) U.S. Cl.
CPC ........ *A61B 5/7435* (2013.01); *A61B 5/7455* (2013.01); *G08B 21/22* (2013.01); *A61B 5/4818* (2013.01); *A61B 2505/07* (2013.01); *A61B 2562/0247* (2013.01); *A61B 2562/0271* (2013.01); *G08B 21/0461* (2013.01)

(56) References Cited

U.S. PATENT DOCUMENTS

| | | | |
|---|---|---|---|
| 2008/0132808 A1* | 6/2008 | Lokhorst | A61B 5/447 600/595 |
| 2012/0053424 A1 | 3/2012 | Kenalty et al. | |
| 2014/0089673 A1* | 3/2014 | Luna | H04L 63/0861 713/186 |
| 2014/0259417 A1* | 9/2014 | Nunn | A61G 7/015 5/614 |
| 2014/0298586 A1 | 10/2014 | Van Thienen et al. | |
| 2015/0128353 A1 | 5/2015 | Kildey | |
| 2015/0164409 A1 | 6/2015 | Benson et al. | |
| 2015/0199919 A1* | 7/2015 | Ander | G09B 21/009 340/4.12 |
| 2015/0319138 A1* | 11/2015 | Yan | H04L 63/145 726/11 |
| 2017/0042340 A1* | 2/2017 | Chacon | A61G 5/14 |
| 2018/0116415 A1* | 5/2018 | Karschnik | A61M 21/02 |

FOREIGN PATENT DOCUMENTS

| | | |
|---|---|---|
| CN | 204427339 U | 7/2015 |
| CN | 204798580 U | 11/2015 |
| CN | 105318503 A | 2/2016 |
| CN | 205107049 U | 3/2016 |
| CN | 105771092 A | 7/2016 |
| CN | 105828670 A | 8/2016 |
| CN | 105832348 A | 8/2016 |
| CN | 105962896 A | 9/2016 |
| CN | 205758139 U | 12/2016 |
| GB | 2520169 A | 5/2015 |
| KR | 10-2016-0080898 A | 7/2016 |
| WO | 2011/094448 A1 | 8/2011 |
| WO | 2016/107121 A1 | 7/2016 |
| WO | 2016/179794 A1 | 11/2016 |

* cited by examiner

SMART BED SYSTEMS AND METHODS OF OPERATION THEREOF

1. TECHNICAL FIELD

At least one embodiment of the present invention provides bed systems. More particularly, smart bed systems monitoring physiological activities and remotely control appliances.

2. DESCRIPTION OF THE RELATED ART

Conventional mattresses usually improve the quality of sleep by modifying the structures, softness, flexibility, materials, and supporting strength to release the stress. However, none of these mattresses tries to monitor and record sleep and regulate ambient environment, such as temperature, humidity, light, etc.

Wearable or attachable devices in combination with the conventional mattresses have been developed to monitor sleep. However, most of these devices are designed for medical uses in hospitals, such as to diagnose sleep disorders and identify the causes of poor sleep quality. These devices cannot be used at home.

Recently, mattresses with pressure sensors have been developed to identify the presence of any user on the mattresses by detecting the pressure change induced by on-mattress activities. Nevertheless, such designs are fragile to electromagnetic interference.

SUMMARY

Some embodiments of the present invention provide smart bed systems having resistance to electromagnetic interference. The smart bed systems monitor activities to automatically remotely control appliances to regulate ambient environment and improve the quality of sleep based on the scenario. The smart bed systems also provide several functions, such as anti-snoring assistance, vibration-based alarm, and automatic night light. The smart bed systems comprise a mattress, a sensing layer disposed in the mattress, a Schumann resonance generator disposed in the mattress, a controller disposed in the mattress and electrically connected with the sensing layer and the Schumann resonance generator respectively, a first Bluetooth transceiver disposed in the mattress and electrically connected to the controller, and a power supply and management system disposed in the mattress and electrically connected to the controller. Furthermore, the smart bed systems comprise a smart device having an application and a second Bluetooth transceiver disposed therein. The sensing layer is configured to generate physiological data based on the activities of a user. The controller is configured to determine the presence of the user on the mattress and output a control signal based on a command. The smart device is configured to receive and display the physiological data and the application is configured to analyze the physiological data and output the command to the controller.

Some embodiments of the present invention provide methods of operation for smart bed systems. The methods comprises a step of providing the smart bed system disclosed in the previous embodiment; a step of providing a QR code to launch an application of a smart device; a step of selecting a sleep tracking mode, a sleep history mode, a bed configuration mode, a smart home mode, an alarm mode, a night light mode, or an anti-snoring mode in the application; a step of obtaining physiological data based on the activities of a user by the sensing layer; a step of determining the presence of the user on the mattress based on the physiological data by the controller; a step of generating a command to the controller based on the physiological data by the application; and a step of generating a control signal to control a vibration motor, a Schumann resonance generator, a motorized bed frame, and at least one infrared radiation (IR) appliance.

DESCRIPTION OF THE PREFERRED EMBODIMENTS

Figure 1:
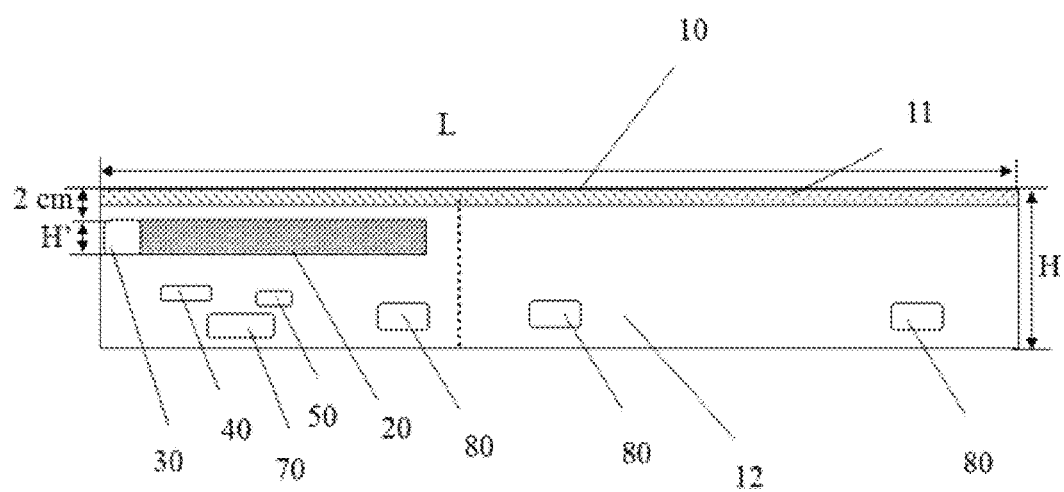
FIG. 1 is the cross-sectional view of a mattress, in accordance with some embodiments of the present invention.
Figure 2:
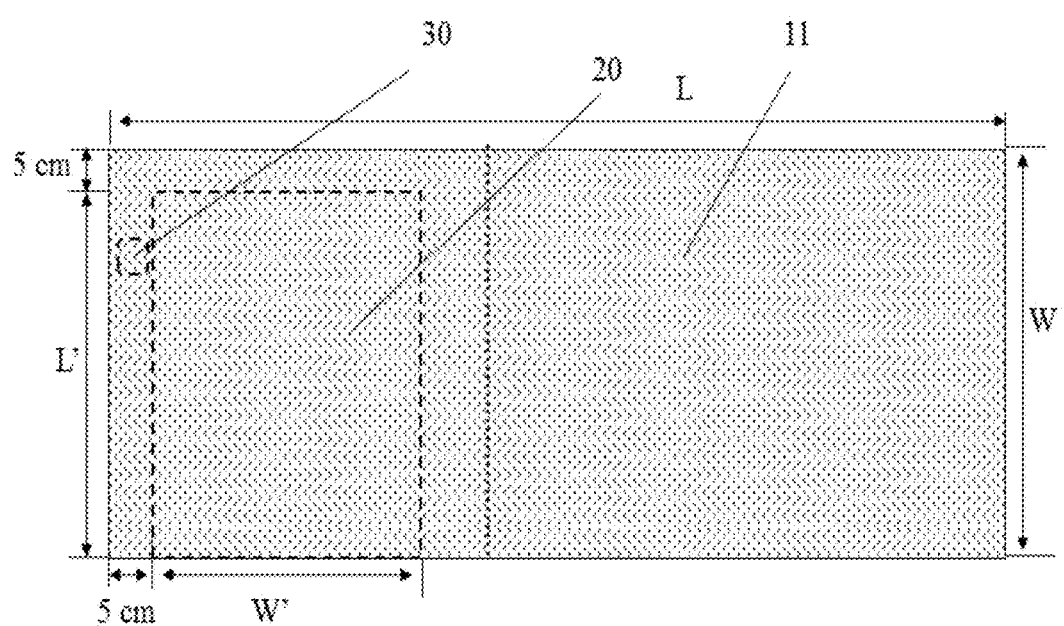
FIG. 2 is the top view of a mattress, in accordance with some embodiments of the present invention.
Figure 3:
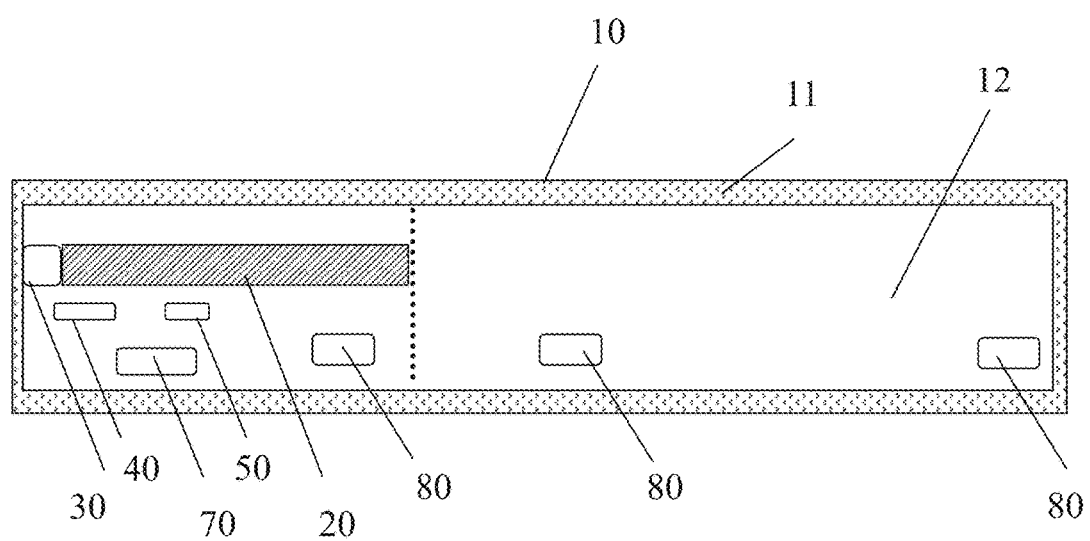
FIG. 3 is another cross-sectional view of a mattress, in accordance with some embodiments of the present invention.
Figure 4:
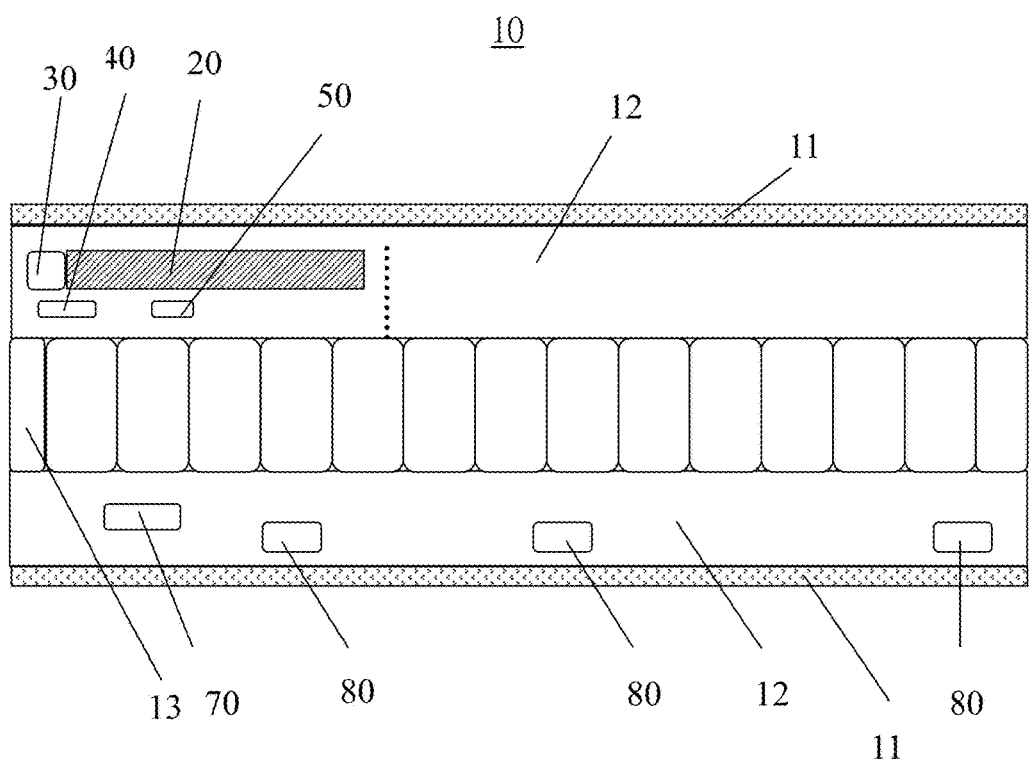
FIG. 4 is yet another cross-sectional view of a mattress, in accordance with some embodiments of the present invention.
Figure 5:
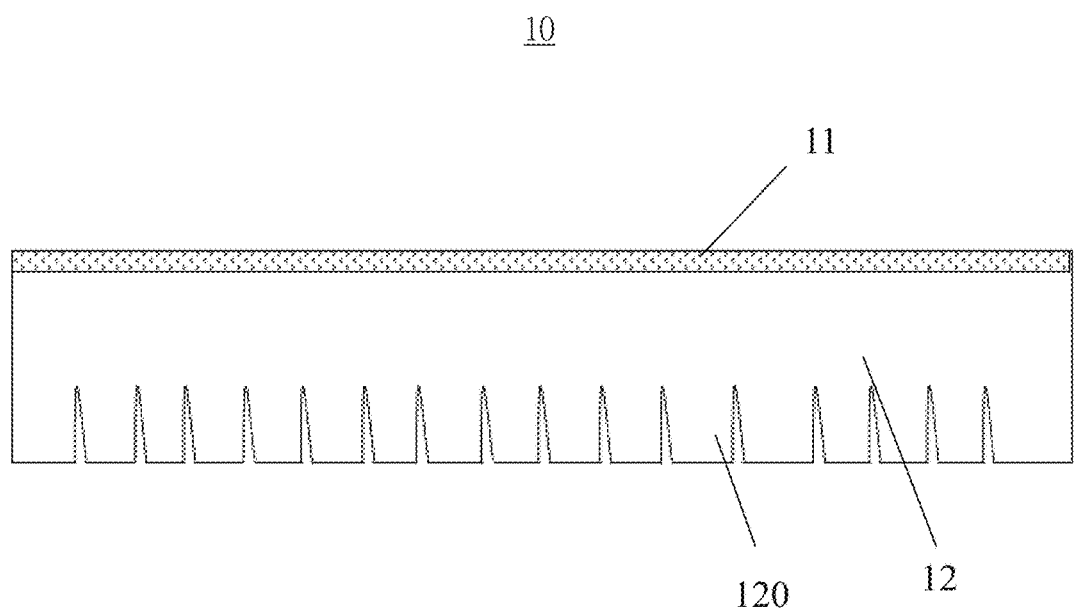
FIG. 5 illustrates a mattress topper with grooves, in accordance with some embodiments of the present invention.

Please refer to FIG. 1, FIG. 2, FIG. 3, and FIG. 4. FIG. 1 is the cross-sectional view of a mattress, in accordance with some embodiments of the present invention; FIG. 2 is the top view of a mattress, in accordance with some embodiments of the present invention; FIG. 3 is another cross-sectional view of a mattress, in accordance with some embodiments of the present invention; FIG. 4 is yet another cross-sectional view of a mattress, in accordance with some embodiments of the present invention. As illustrated in FIG. 1 and FIG. 3, the mattress 10 comprises a cover 11 and a mattress topper 12. The cover 11 is disposed on or wrapping the mattress topper 12. The cover 11 is made of thermoplastic polyurethanes (TPU), a water-proof material for medical use. The mattress topper 12 is made of high density foam, which provides strong elasticity and durability while fits and supports the body in a soft and comfortable manner. As illustrated in FIG. 5, the mattress topper 12 comprises multiple grooves 120 at the back. The grooves 120 render the mattress topper 12 able to be folded and provide good ventilation to the mattress topper 12.

As illustrated in FIG. 1 and FIG. 2, the specification of the mattress 10 in some embodiments is 191 cm in length (L), 91 cm in width (W), and 10 cm in height (H). The specification of the sensing layer 20 is 85 cm in length (L'), 50 cm in width (W'), and 2.2 cm in height (H'). The sensing layer 20 is disposed 2 cm above the mattress 10 with 5 cm of margin at top and right.

Please refer to FIG. 4. FIG. 4 is another cross-sectional view of a mattress, in accordance with some embodiments of the present invention. As illustrated in FIG. 4, the mattress 10 also comprises a cover 11 and a mattress topper 12. FIG. 4 further comprises a mattress base 13 disposed under the mattress topper 12 to support the body weight of users. The mattress base 13 may comprise Marshall coils, Marshall coils in honeycombed array, Bonnell coils, continuous coils, or coils made of high carbon steel. A pair of the covers 11 and a pair of the mattress toppers 12 are symmetrically disposed on the opposite sides of the mattress base 13.

Moreover, the covers 11 usually are made of materials with good ventilativeness and moisture-wicking ability which are friendly to skins. The exemplary material for the covers 11 includes cotton, tencel, wool, and silk. The mattress topper 12 may comprise at least one layer, in which the layer is made of one material selected from the group consisting of sponge, latex, nonwoven fabric, cellucotton, cotton impregnated with phenolic resin, cotton blanket, memory foam, coconut fibre, bincho charcoal foam, woven cotton, or foam. Each of the above materials has different characteristics and functions. For example, latex, a natural material, shows high elasticity, density, and supporting strength while provides good ventilation. Memory foam, a temperature sensitive material which softens in reaction to high temperature but hardens in reaction to low temperature, molds and fits the shape of body. Nonwoven fabric is a ventilating, soft, easy-to-cut, foldable, electrically isolative, strong, and anti-microbial material. The pores and channels render cellucotton ventilative, thermal, and fluffy. Cotton impregnated with phenolic resin may be used to replace sponge to provide better abilities in color-fixation, elasticity, and wash-resistance. Foam is good at absorption and ventilation. Cool gel can be used to regulate the body temperature without the change in viscosity in reaction to temperature. Bincho charcoal foam is dust mite-proof and anti-microbial, and may be used to remove odors. Based on the consideration of comfortability, ventilativeness, fitness, and supporting strength, one may select multiple layers to form the mattress topper 12.

Figure 7:
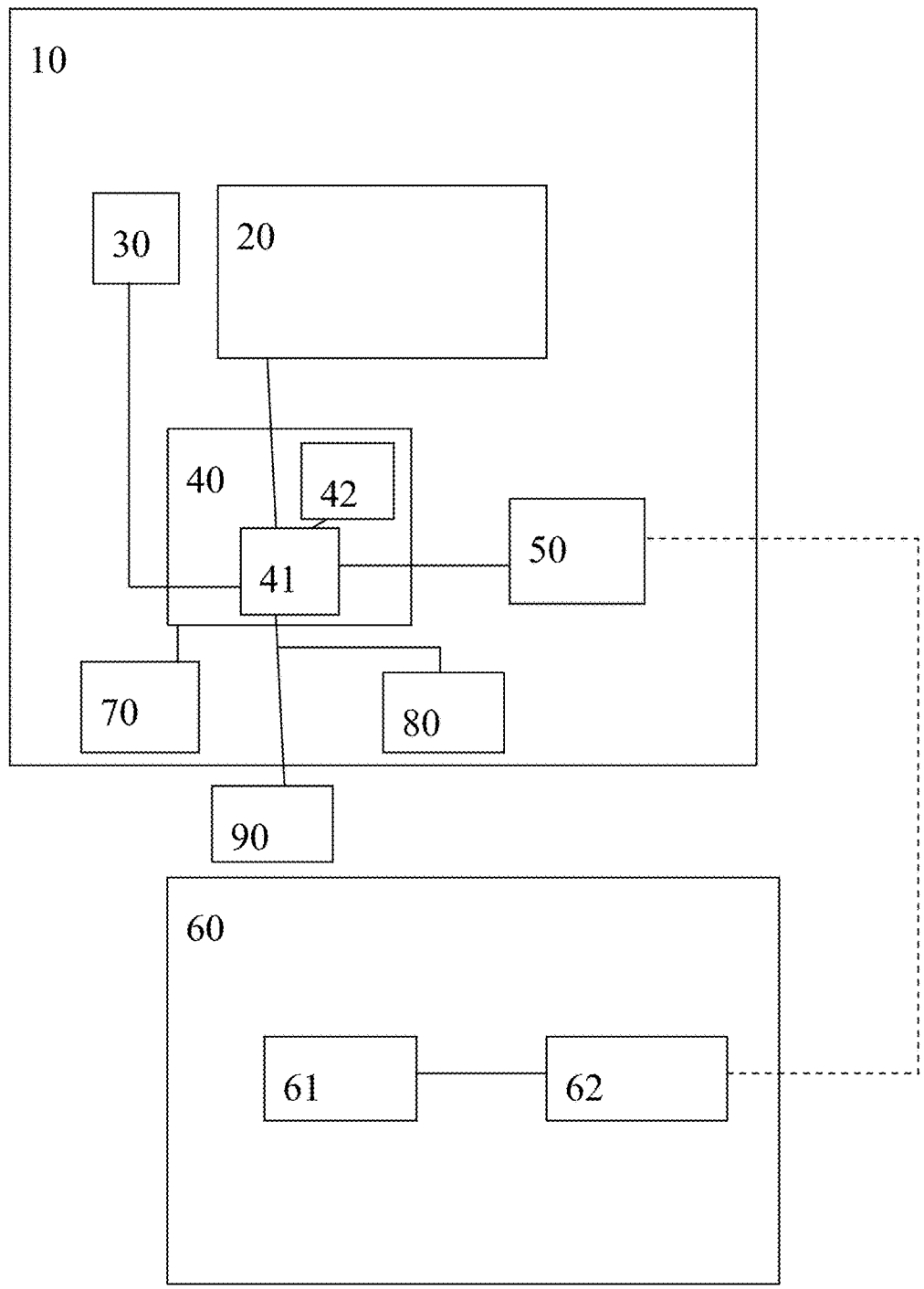
FIG. 7 is a schematic diagram illustrating a smart bed system, in accordance with some embodiments of the present invention.

Please refer to FIG. 1, FIG. 2, FIG. 3, and FIG. 7. FIG. 7 is a schematic diagram illustrating a smart bed system, in accordance with some embodiments of the present invention. The smart bed system 1 comprises a mattress 10, a sensing layer 20 disposed in a mattress topper 12 of the mattress 10, a Schumann resonance generator 30 disposed in a mattress topper 12 of the mattress 10, a controller 40 disposed in a mattress topper 12 of the mattress 10 and electrically connected with the sensing layer 20 and the Schumann resonance generator 30 respectively, a first Bluetooth transceiver 50 disposed in a mattress topper 12 of the mattress 10 and electrically connected to the controller 40, and a power supply and management system 70 disposed in the mattress 10 and electrically connected to the controller 40. Furthermore, the smart bed system 1 comprises a smart device 60 having an application 61 and a second Bluetooth transceiver 62 disposed therein, in which the application 61 is electrically connected with the second Bluetooth transceiver 62.

The controller 40 comprises a processor 41 and a memory device 42, in which the processor 41 is connected with the memory device 42. The processor 41 is configured to receive and analyze physiological data to determine the presence of a user on the mattress 10, and to receive a command to generate a control signal. The memory device 42 is configured to store the physiological data.

The first Bluetooth transceiver 50 and the second Bluetooth transceiver 62 may be one selected from the group consisting of Bluetooth 1.0, Bluetooth 1.0B, Bluetooth 2.0+ enhanced data rate (EDR), Bluetooth 2.1+EDR, Bluetooth 3.0+high speed (HS), and Bluetooth 4.0. The smart device 60 may be one selected from the group consisting smart phones, tablets, and PDAs. The smart device 60 paired with the sensing layer 20 through Bluetooth. The Bluetooth technology provides a working range of 30 M in open area or 10-20 M in house without the requirement of external internet.

The smart bed system 1 also comprises at least one vibration motor 80 disposed in the mattress 10 and electrically connected to the controller 40.

Figure 6:
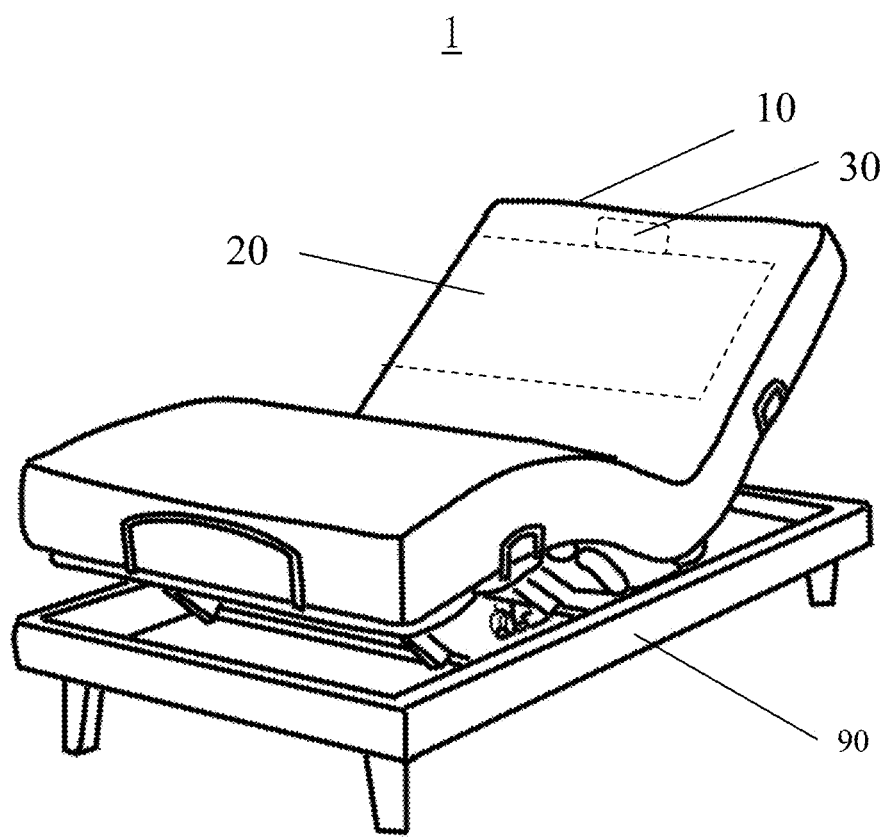
FIG. 6 is a schematic diagram illustrating a motorized bed frame, in accordance with some embodiments of the present invention.

Please refer to FIG. 6. FIG. 6 is a schematic diagram illustrating a motorized bed frame, in accordance with some embodiments of the present invention. The smart bed systems 1 in some embodiments further comprises a motorized bed frame 90 under the mattress 10.

Please refer to FIG. 7. The sensing layer 20 detects the activities of users to generate physiological data. The physiological data may comprise one selected from the group consisting of a heart rate value, a pulse wave data, a blood pressure value, sleep analysis data (e.g., awake time, light sleep, deep sleep), a respiratory rate value, and the combination thereof. The controller 40 is configured to receive and analyze physiological data to determine the presence of a user on the mattress 10. The controller 40 transmits the physiological data to the smart device 60 through the first Bluetooth transceiver 50. The smart device 60 then receives and displays the physiological data. The application 61 sends a command to the controller 40 through the wireless connection between the first Bluetooth 50 transceiver and the second Bluetooth transceiver 62. The command may be a sleep tracking command, a sleep history command, a bed configuration command, a smart home command, an alarm command, a night light command, or an anti-snoring command. The controller 40 then generates a control signal based on the received command. The control signal may be a sleep tracking signal, a sleep history signal, a bed configuration signal, a smart home signal, an alarm signal, a night light signal, or an anti-snoring signal.

The smart device 60 turns on the Schumann resonance generator 30 when a user is on the mattress 10, and turns off the Schumann resonance generator 30 when the user is off the mattress 10. The Schumann resonance generator 30 is configured to generate low frequency waves at 7~8 Hz (i.e., the Schumann wave). The low frequencies wave resemble to the alpha waves of a brain in the state of peace, calm, and quiet. Therefore, the Schumann wave may promote relaxation of the user through oscillation.

Figure 8:
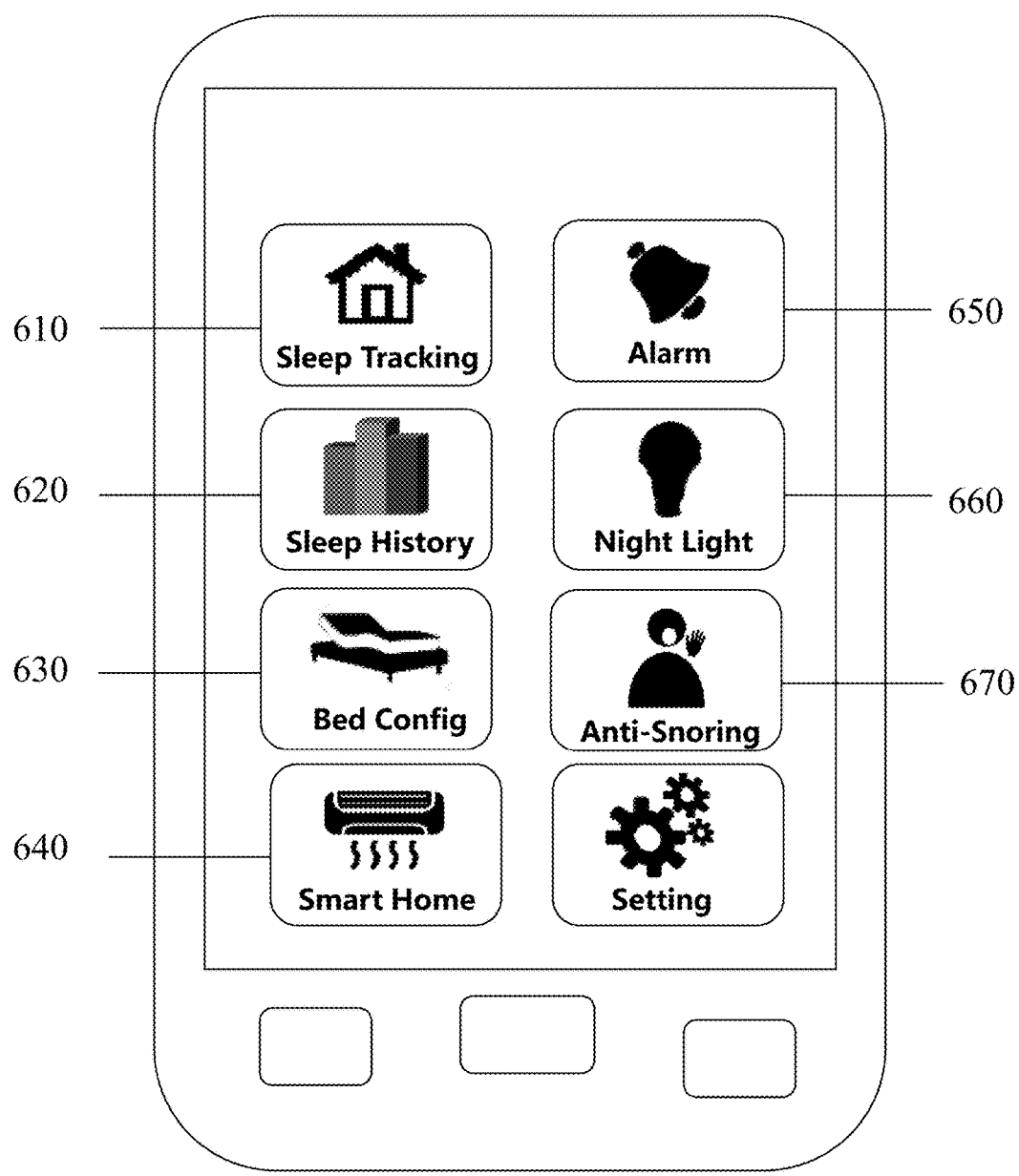
FIG. 8 is a schematic diagram illustrating an application having several modes, in accordance with some embodiments of the present invention.

Please refer to FIG. 8. FIG. 8 is a schematic diagram illustrating an application having several modes, in accordance with some embodiments of the present invention. The application 61 comprises a sleep tracking mode 610, a sleep history mode 620, a bed configuration mode 630, a smart home mode 640, an alarm mode 650, a night light mode 660, and an anti-snoring mode 670. The sleep tracking mode 610 displays heart rate values in a real-time manner or a graph depicting the history of respiratory rate. The sleep history mode 620 collects one selected from the group consisting of the duration of sleep, the duration of awake time, the duration of light sleep, the duration of deep sleep, the duration on bed, the duration off bed, the ratio among awake time/light sleep/deep sleep, the frequency of tossing and turning, and the combination thereof on a daily basis, a weekly basis, or a monthly basis. The bed configuration mode 630 provides options for the type of massage, the strength of massage, the linkage type of massage, and the part of massage. The smart home mode 640 provides configuration to perform one action selected from the group consisting of designing a scenario to remotely control appliances, connecting a new appliance, and adding a new smart socket. The alarm mode 650 provides configuration to set the time of an alarm which wake the user by vibration. The night light mode 660 provides configuration to set the activation time of a night light module which automatically activates the night light when the user is absent on the mattress and deactivates the night light when the user is on the mattress. The anti-snoring mode 670 automatically induces vibration or adjusts the height when any snore is over 65 decibels, in a period of time, or in a pre-determined frequency.

The smart bed system 1 uses optical fibers as sensors which provide high sensitivity and accuracy to detect activities such as breathes, heart rates, pulse waves, blood pressures, sleep analysis, temperatures, humidity in a non-invasive manner. The optical fibers are insensitive to electromagnetic interference (EMI). The optical fibers transmit data in long-distance with minimum signal loss. Moreover, the optical fibers are temperature resistant and generate no spark or static electricity during transmission. Moreover, the smart bed system 1 and the smart device 60 have bidirectional communication through a Bluetooth network. The smart bed system 1 therefore may monitor sleep, remotely control appliances based on the physiological data, and regulate the switch of infrared radiation (IR) appliances through smart sockets to improve the ambient environment to promote sleep. The smart bed system 1 also provides functions such as vibration-based alarm, automatic night light, and anti-snoring assistance.

Figure 29:
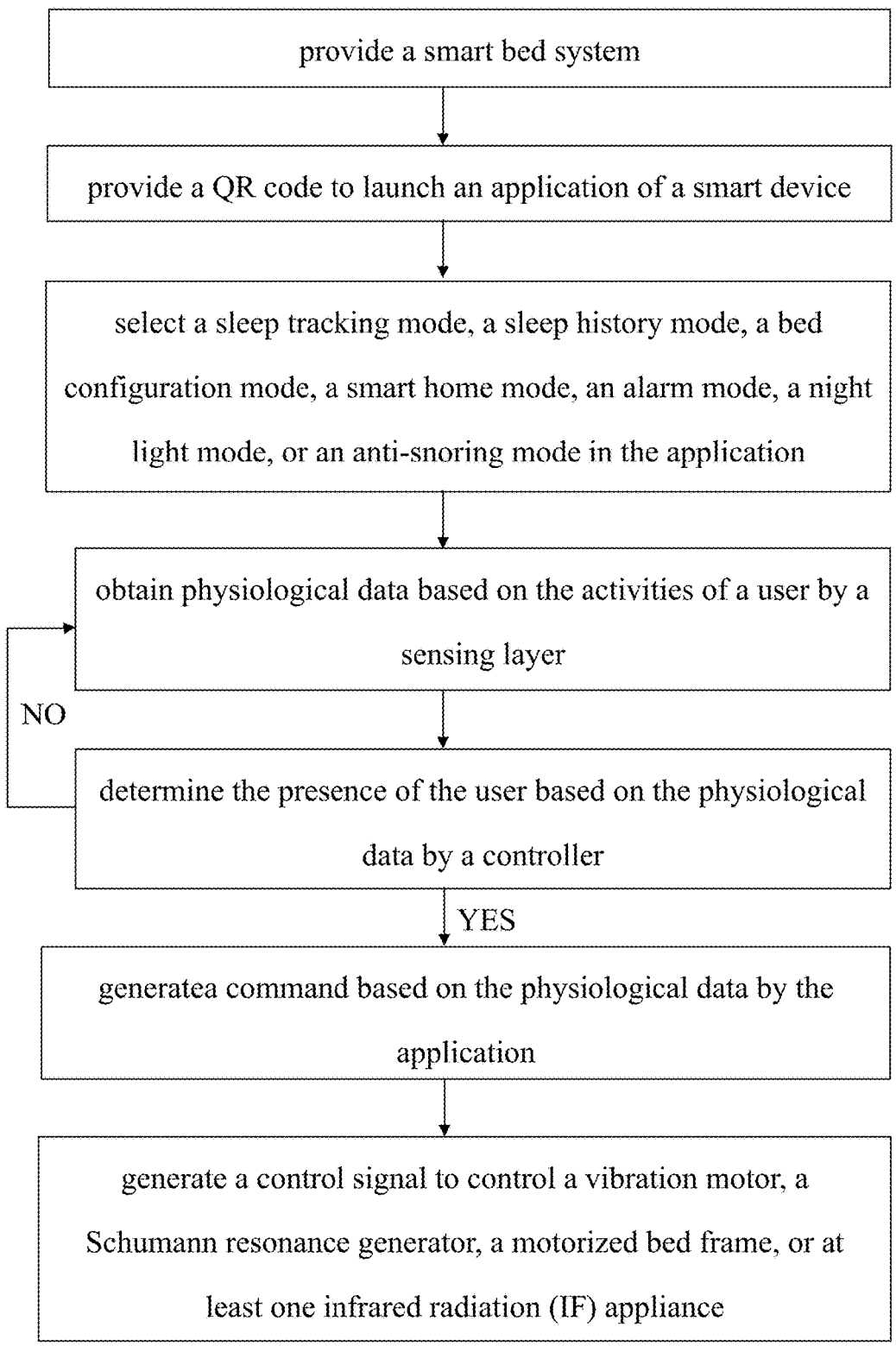
FIG. 29 is a flow chart illustrating an operating method of smart bed systems, in accordance with some embodiments of the present invention.

Please refer to FIG. 29. FIG. 29 is a flow chart illustrating an operating method of smart bed systems, in accordance with some embodiments of the present invention. The operating method of smart bed systems 1 comprises a step A of providing the smart bed system disclosed in the previous embodiment; a step B of providing a QR code to launch an application of a smart device; a step C of selecting a sleep tracking mode, a sleep history mode, a bed configuration mode, a smart home mode, an alarm mode, a night light mode, or an anti-snoring mode in the application; a step D of obtaining the physiological data based on the activities of a user by the sensing layer; a step E of determining the presence of the user on the mattress based on the physiological data by the controller; a step F of generating a command to the controller based on the physiological data by the application; and a step G of generating a control signal to control a vibration motor, a Schumann resonance generator, a motorized bed frame, and at least one IR appliance by the controller. If the user is absent from the mattress and the determination result is therefore negative in step E, repeat step D. If the user is present on the mattress, moves forward to step F.

The at least one IR appliance in step G is a TV, a fan, an air conditioner, an air cleaner, a speaker, an LED lighting, or a coffee machine.

Figure 9:
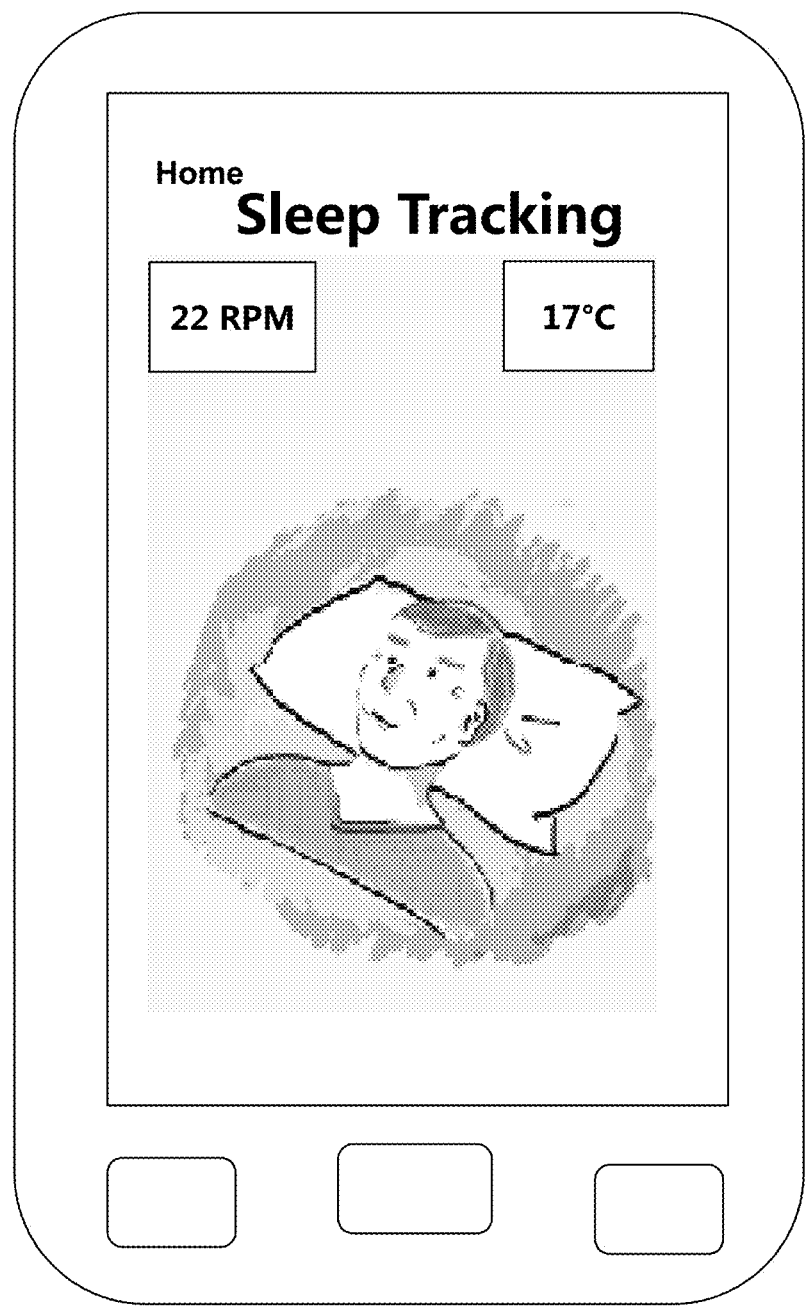
FIG. 9 is a schematic diagram illustrating a sleep tracking mode, in accordance with some embodiments of the present invention.
Figure 10:
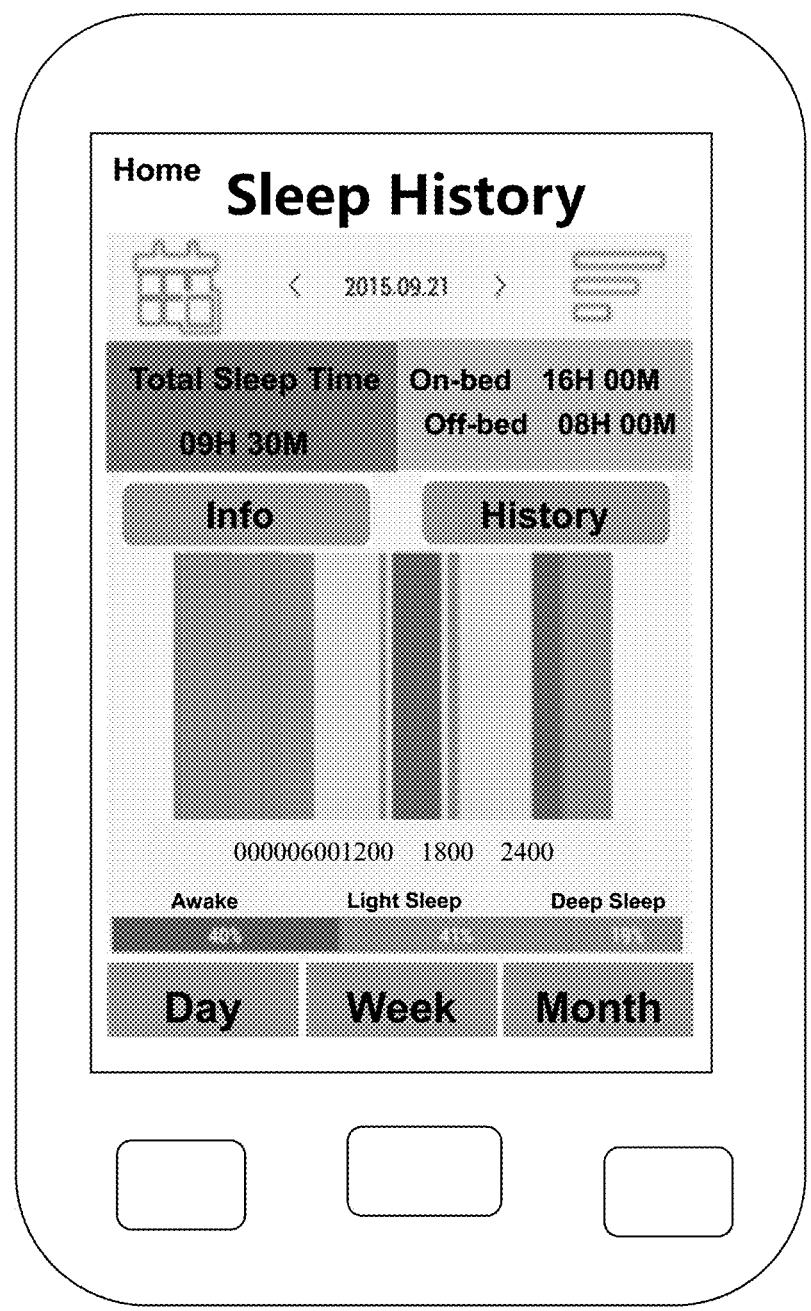
FIG. 10 is a schematic diagram illustrating a page of the sleep tracking mode, in accordance with some embodiments of the present invention.
Figure 11:
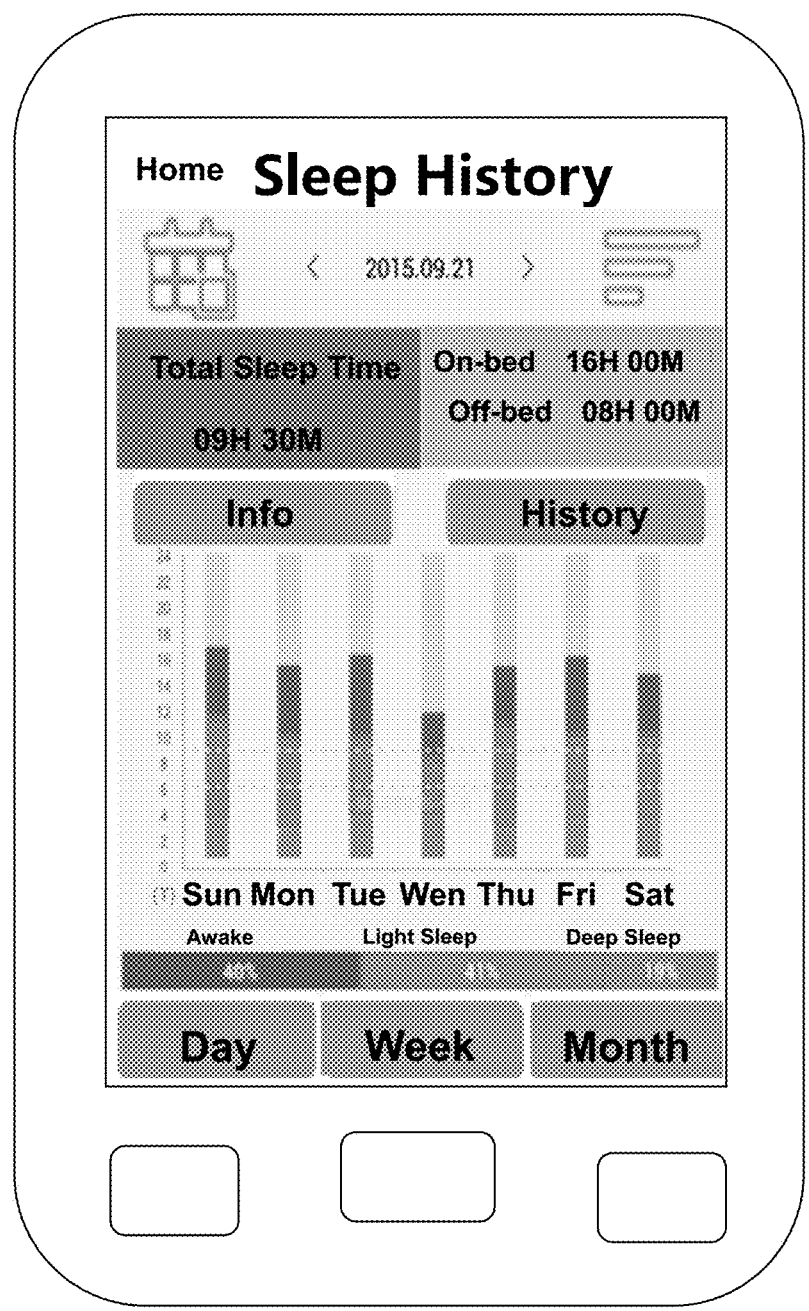
FIG. 11 is a schematic diagram illustrating another page of the sleep tracking mode, in accordance with some embodiments of the present invention.
Figure 12:
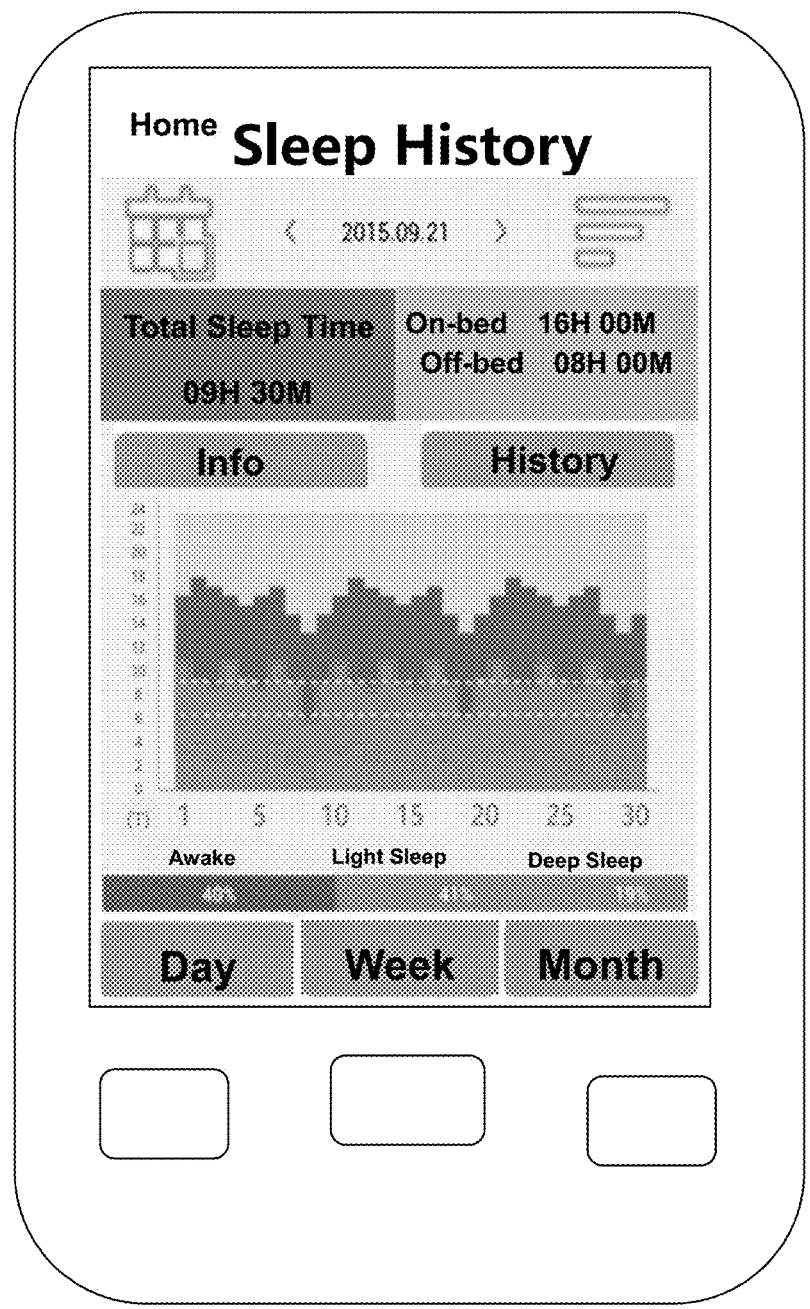
FIG. 12 is a schematic diagram illustrating yet another page of the sleep tracking mode, in accordance with some embodiments of the present invention

The following embodiments provide a wide variety of operating procedures of modes in the application 61. Please refer to FIG. 7, FIG. 8, FIG. 9, FIG. 10, FIG. 11, and FIG. 12. FIG. 9 is a schematic diagram illustrating a sleep tracking mode; FIG. 10 is a schematic diagram illustrating a page of the sleep tracking mode; FIG. 11 is a schematic diagram illustrating another page of the sleep tracking mode; and FIG. 12 is a schematic diagram illustrating yet another page of the sleep tracking mode.

A user may use a smart device 60 to scan a QC code to activate the application 61, and select the sleep tracking mode 610 to generate a sleep tracking command. The user then goes to the mattress 10 for sleep. During the sleep, the sensing layer 20 generates physiological data based on the activities of the user and transmits to the memory device 42 of the controller 40 for storage. The processor 41 in the controller 40 determines the presence of the user on the mattress 10 based on the physiological data and transmits such physiological data to the application 61 via the wireless connection between the first Bluetooth transceiver 50 and the second Bluetooth transceiver 62. The application 61 then generates a sleep tracking command and transmits to the controller 40 through the wireless connection between the first Bluetooth transceiver 50 and the second Bluetooth transceiver 62. Upon the receipt of the sleep tracking command, the processor 41 in the controller 40 generates a sleep tracking signal to retrieve the physiological data (e.g., the heart rate value) and transmit to the sleep tracking mode 610 on the smart device 60 via the wireless connection between the first Bluetooth transceiver 50 and the second Bluetooth transceiver 62. The smart device 60 then timely displays the heart rate value, 22 BPM, of the user as illustrated in FIG. 9.

Figure 28:
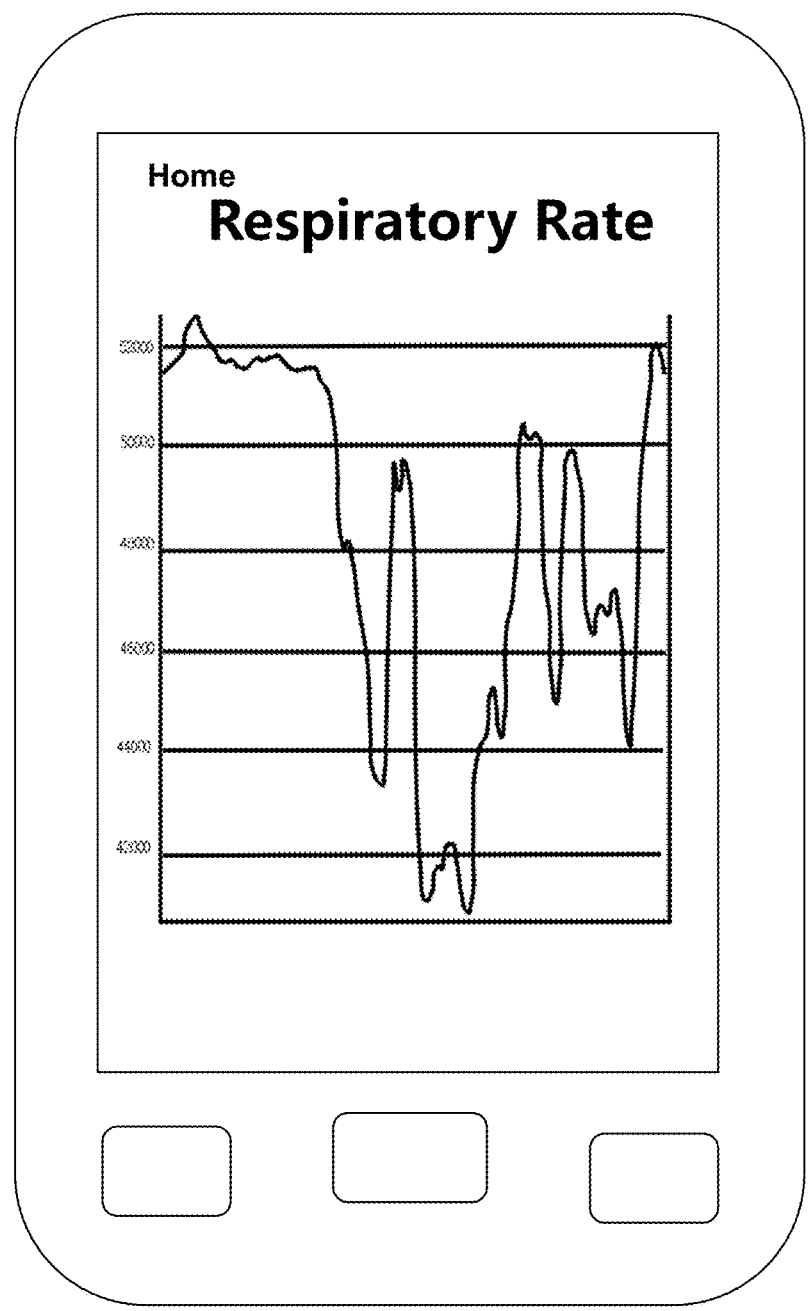
FIG. 28 is a graph depicting the history of respiratory rate, in accordance with some embodiments of the present invention.

Please refer to FIG. 28. FIG. 28 is a graph depicting the history of respiratory rate, in accordance with some embodiments of the present invention. The sleep tracking mode 610 of the application 61 can also utilize the sensing layer 20 to detect respiratory rate. The detected respiratory rate values may then be consolidated into one graph.

A user may select sleep history mode 620 to generate a sleep history command to the controller 40 through the wireless connection between the first Bluetooth transceiver 50 and the second Bluetooth transceiver 62. Upon the receipt of the sleep history command, the processor 41 in the controller 40 generates a sleep history signal to retrieve the physiological data and transmit to the sleep history mode 620 on the smart device 60. The sleep history mode 620 collects one selected from the group consisting of the duration of sleep, the duration of awake time, the duration of light sleep, the duration of deep sleep, the duration on bed, the duration off bed, the ratio among awake time/light sleep/deep sleep, the frequency of tossing and turning, and the combination thereof on a daily basis, a weekly basis, or a monthly basis, and display such data on the smart device 60. As illustrated in FIG. 10, FIG. 11, and FIG. 12, the user may review the statistical data pertaining to the during the sleep, the duration off bed, the duration on bed, the duration of awake time, the duration of light sleep, the duration of deep sleep, and the ratio among awake time/light sleep/deep sleep on a daily basis, a weekly basis, or a monthly basis collected by the sleep history mode 620 to review the quality of sleep. An alternative method to display the ratio among a wake time/light sleep/deep sleep is a pie chart.

Figure 13:
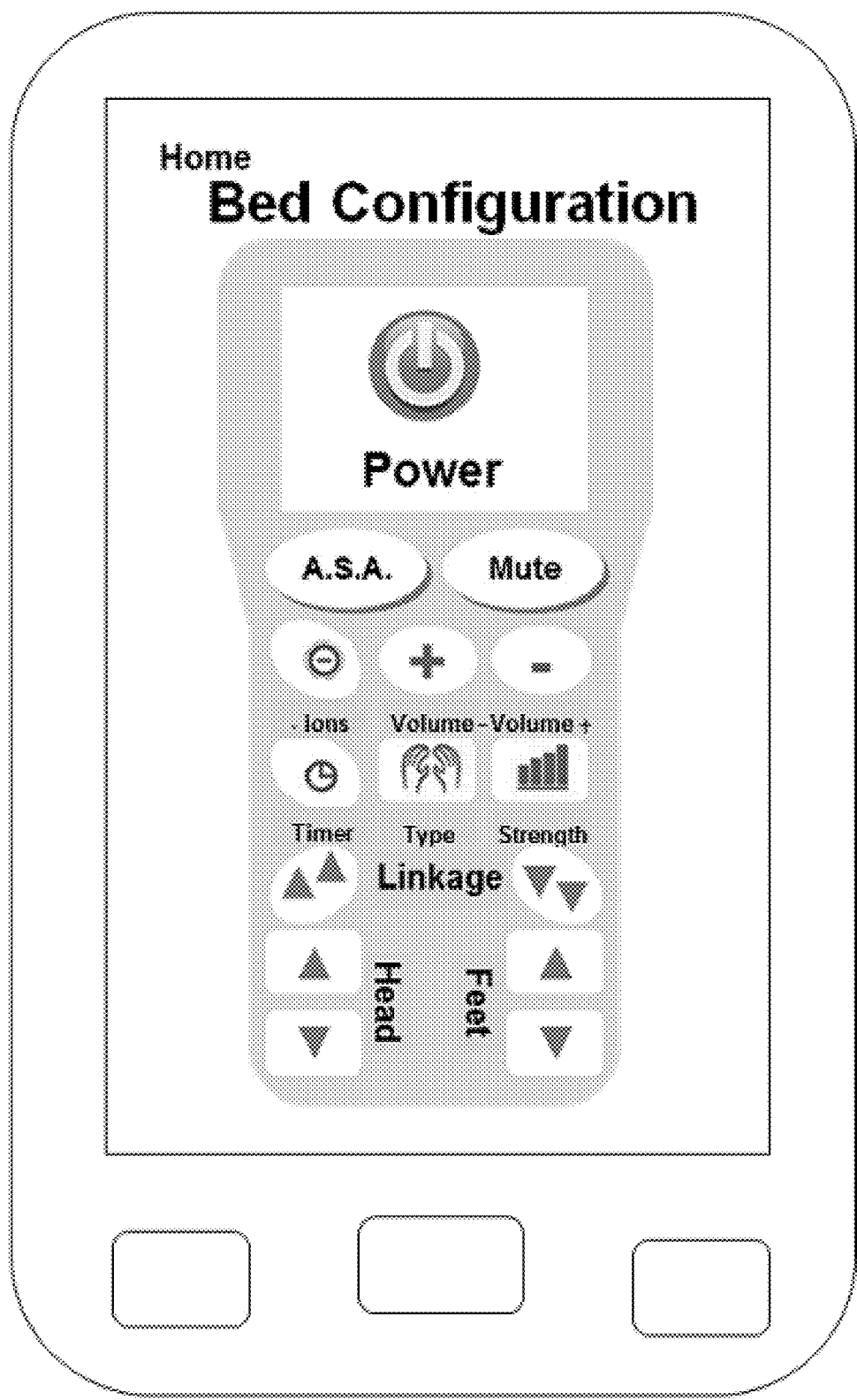
FIG. 13 is a schematic diagram illustrating a bed configuration mode, in accordance with some embodiments of the present invention.

Please refer to FIG. 7, FIG. 8, and FIG. 13. FIG. 13 is a schematic diagram illustrating a bed configuration mode, in accordance with some embodiments of the present invention. Under the bed configuration mode 630, the user may select the type of massage, the strength of massage, the linkage type of massage, and the part of massage to generate a bed configuration command if the smart bed system 10 identifies the presence of the user. Upon the receipt of the bed configuration command, the processor 41 in the controller 40 generates a bed configuration signal to activate the motorized bed frame 70 or at least one vibration motor 80 embedded in the mattress 10. As illustrated in FIG. 13, the user may adjust the type, strength, linkage type, and part (e.g., hands or feet) of massage. Moreover, other options such as volume, mute, negative ions, timer, anti-snoring assistance are also provided.

Figure 25:
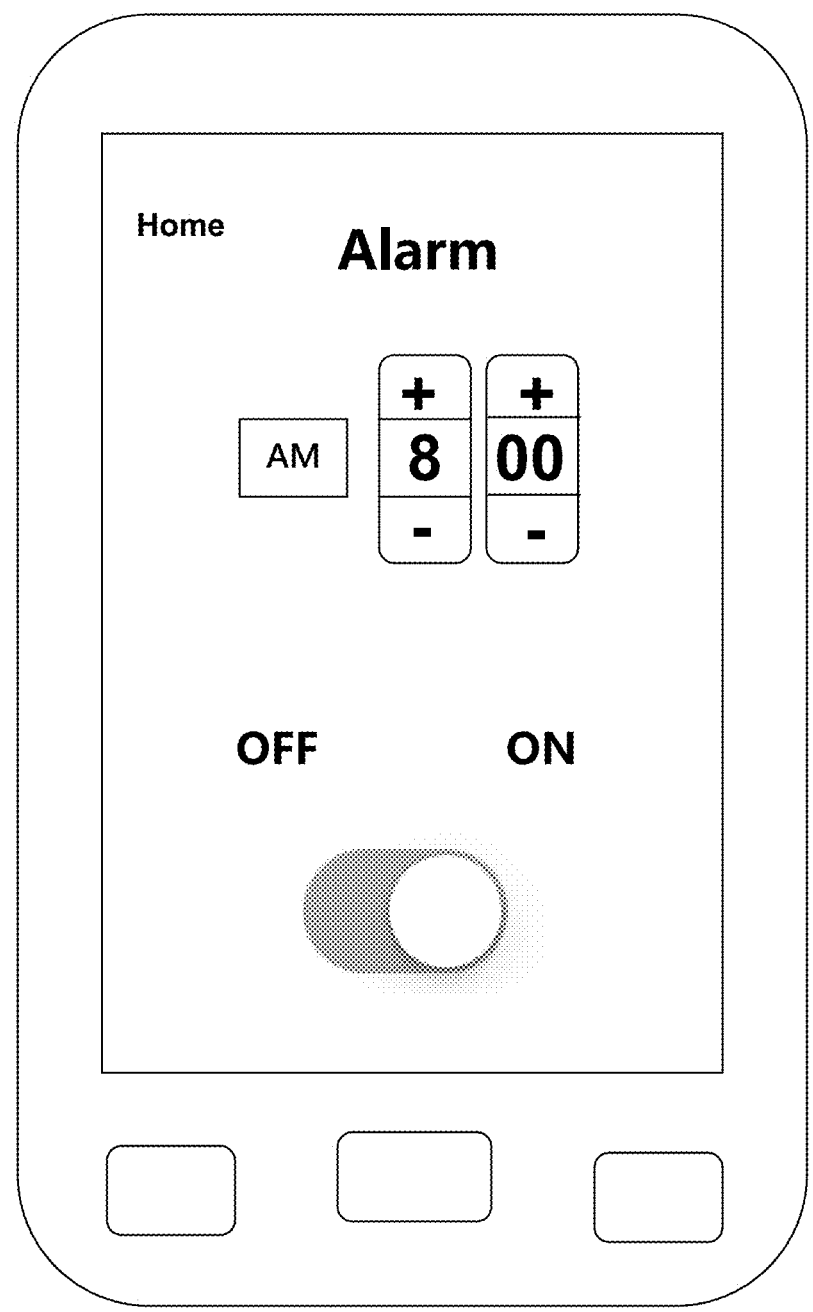
FIG. 25 is a schematic diagram illustrating an alarm mode, in accordance with some embodiments of the present invention.
Figure 30:
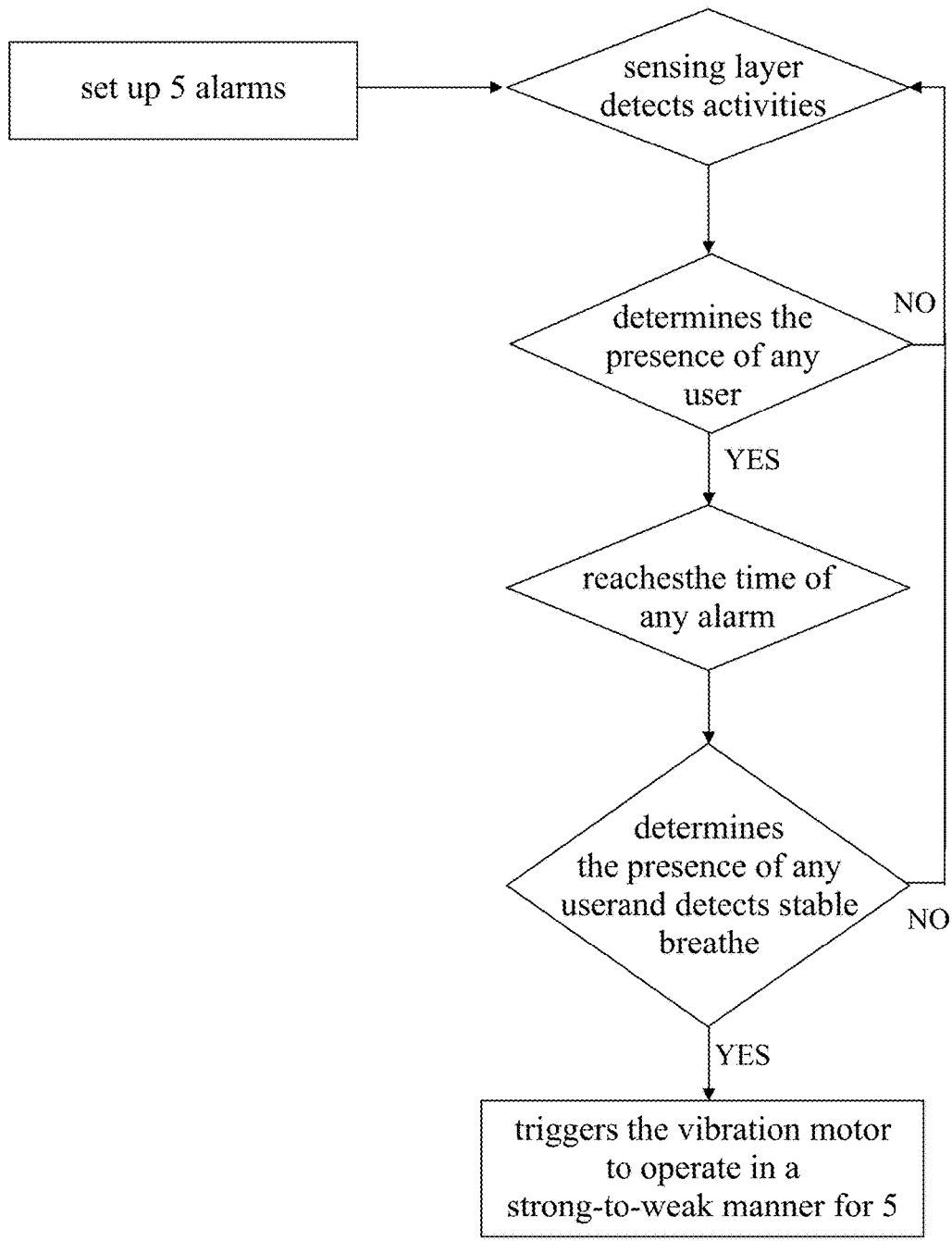
FIG. 30 is a flow chart illustrating an operating procedure of the alarm mode, in accordance with some embodiments of the present invention.

Please refer to FIG. 7, FIG. 8, FIG. 25, and FIG. 30. FIG. 25 is a schematic diagram illustrating an alarm mode, in accordance with some embodiments of the present invention. FIG. 30 is a flow chart illustrating an operating procedure of the alarm mode, in accordance with some embodiments of the present invention. Under the alarm mode 650, the user may set up the time of alarm and generate an alarm command to the controller 40. Upon the receipt of the alarm command, the processor 41 in the controller 40 generates an alarm signal to activate the at least one vibration motor 80 disposed in the mattress 10 at the set time to wake the user, while minimizing surprise to the user or interference to the other people.

FIG. 30 is a flow chart illustrating an operating procedure of the alarm mode, in accordance with some embodiments of the present invention. The alarm mode 650 provides five sets of alarms, each comprises time and day of the week. The five sets of alarms may be synchronized with the alarms app in the smart device 60. After setting an alarm in the alarm mode 650 of the application 61, the alarm command is transmitted to the controller 40 through the Bluetooth connection. The sensing layer 20 then provides physiological data, such as the heart rate value, the pulse wave data, the blood pressure value, sleep analysis data, and the respiratory rate value to the alarm mode 650 of the controller 40 to determine the presence of the user. If the user is present on the mattress, then the alarm mode 650 activates any of the alarms. If the user is absent on the mattress, repeat the procedure of determination. If the user is present on the mattress and any of the alarm is activated, the controller 40 determines whether the user has fallen asleep by detecting the present of stable breathes. If the user has fallen asleep, then sends an alarm signal to trigger the vibration motor 80 to operate in a strong-to-weak manner for 5 minutes. Otherwise, repeat the procedure of determination.

Figure 26:
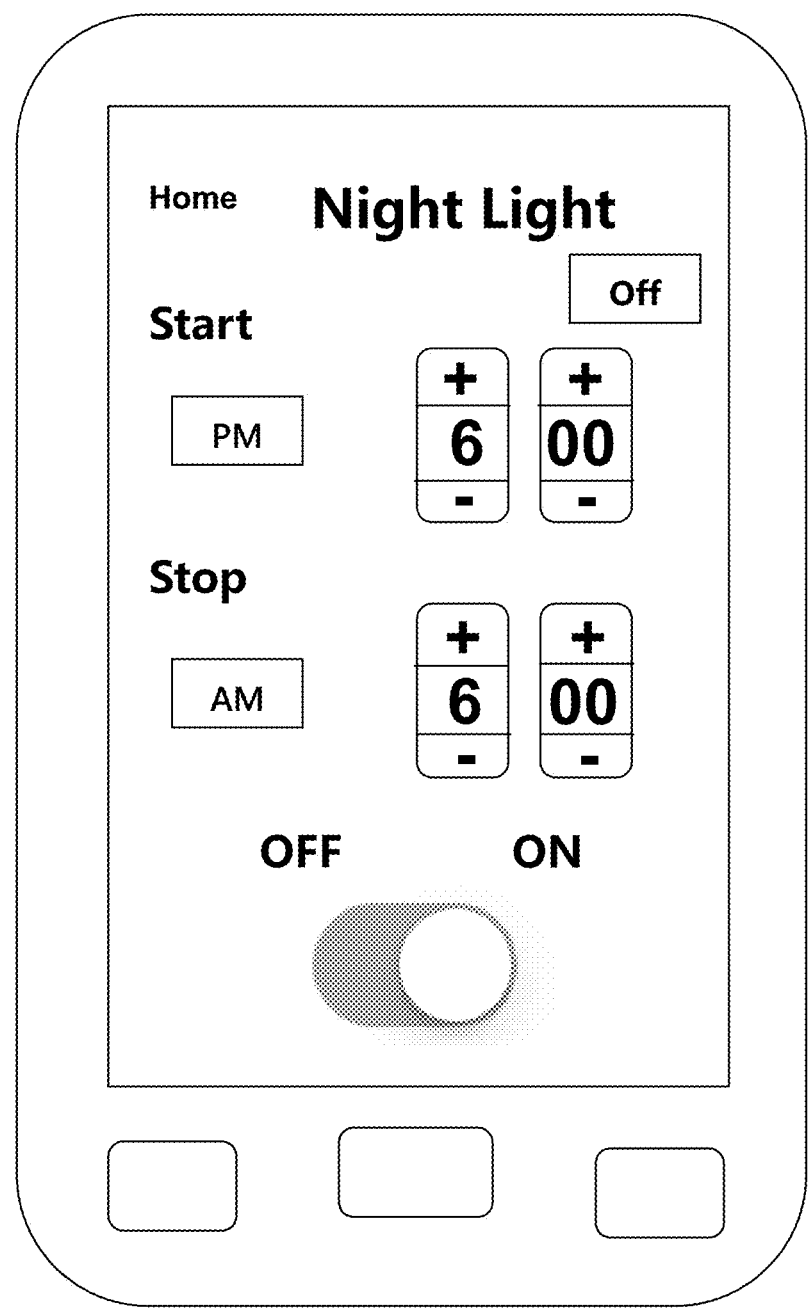
FIG. 26 is a schematic diagram illustrating a night light mode, in accordance with some embodiments of the present invention.
Figure 31:
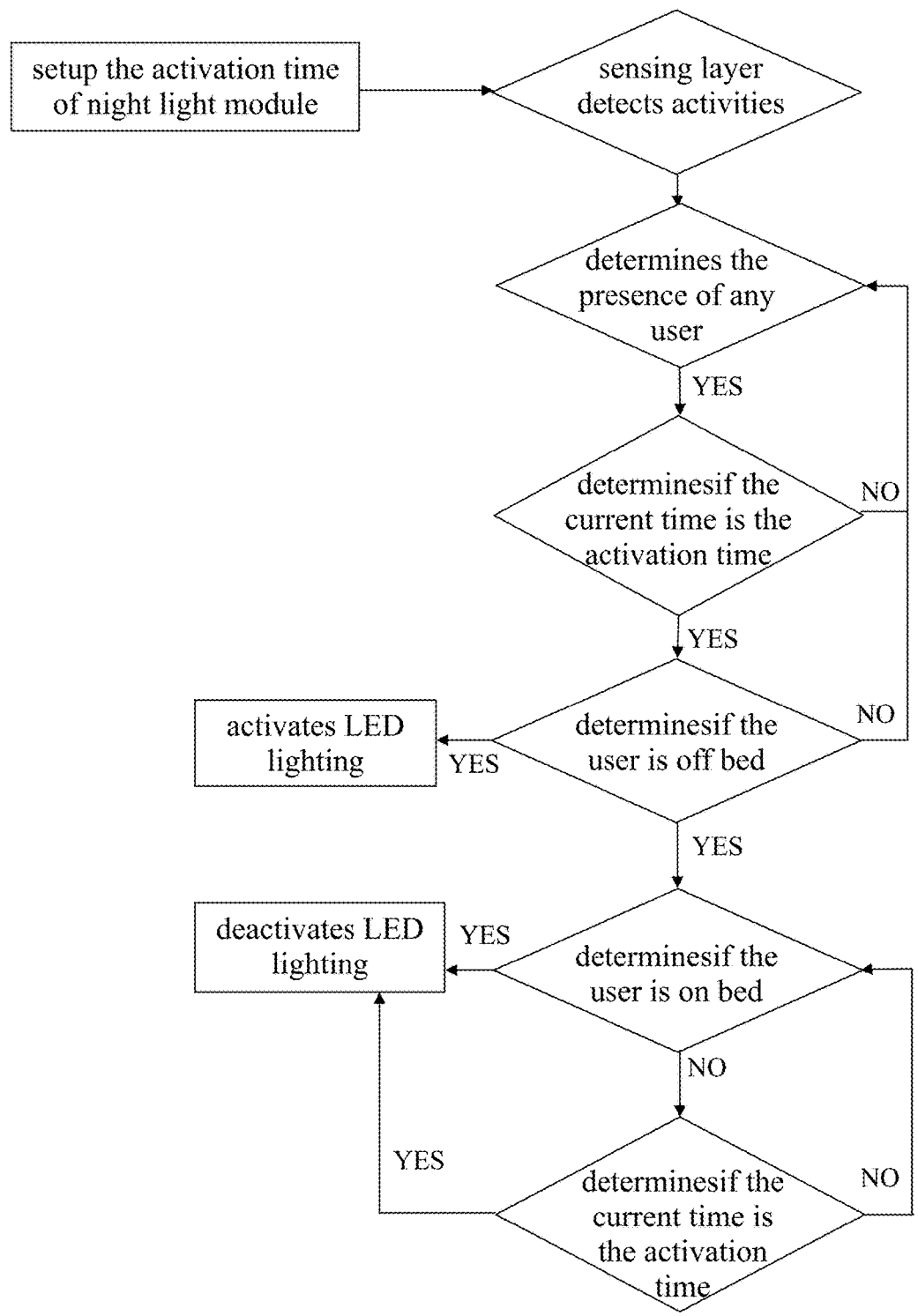
FIG. 31 is a flow chart illustrating an operating procedure of the night light mode, in accordance with some embodiments of the present invention.

Please refer to FIG. 7, FIG. 8, FIG. 26, and FIG. 31. FIG. 26 is a schematic diagram illustrating a night light mode, in accordance with some embodiments of the present invention. FIG. 31 is a flow chart illustrating an operating procedure of the night light mode, in accordance with some embodiments of the present invention. Under the night light mode 660, a user may set the activation time of a night light module to generate a night light command. Upon the receipt of the night light command, the processor 41 in the controller 40 generates a night light signal to automatically activates the night light when the user is absent on the mattress and deactivates the night light when the user is on the mattress during the activation time.

The operating procedure of the night light mode 61 of the application 61 is illustrated in FIG. 31. In the night light mode 660, the user can set the activation time of the automatic night light. Outside of the activation time, activities will not trigger the night light module to react. In the activation time, the night light mode 660 of the application 61 transmits a night light command through a Bluetooth 4.0 connection to the controller 40, and the sensing layer 20 also provides the physiological data such as the heart rate value, the pulse wave data, the blood pressure value, the sleep analysis data, and the respiratory rate value to the controller 40. The controller 40 then determine the presence of the user on the mattress 10 based on the physiological data and fetch such determination result t the night light mode 660 of the smart device 60. Upon the receipt of such determination result, the night light mode 660 generates a night light command to the controller 40. The controller 40 sends out a night light signal to turn off the LED if the user is on the mattress 10. The controller 40 sends out a night light signal to turn on the LED if the user is off the mattress 10. However, after a predetermined period of time, the LED may be turned off by the controller 40 even without the user detected on the mattress 10.

Figure 27:
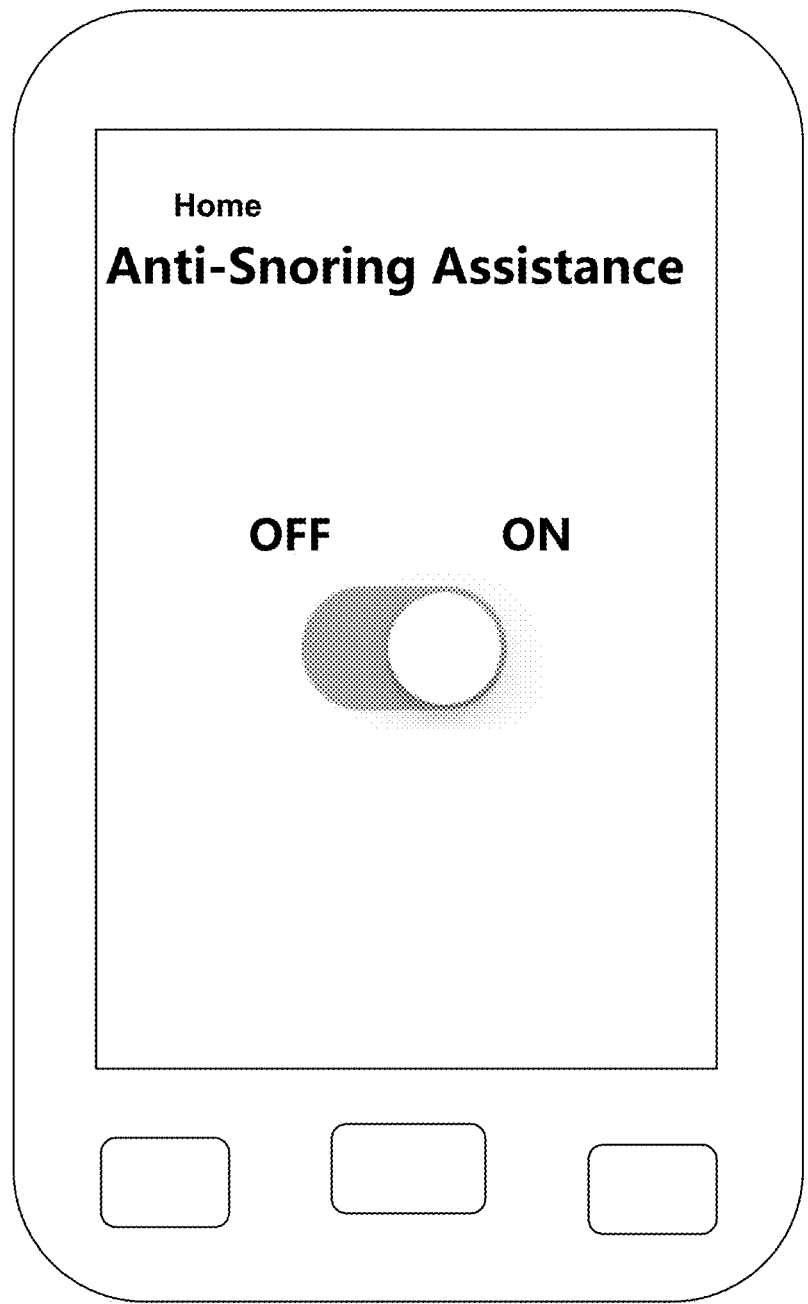
FIG. 27 is a schematic diagram illustrating an anti-snoring mode, in accordance with some embodiments of the present invention.
Figure 32:
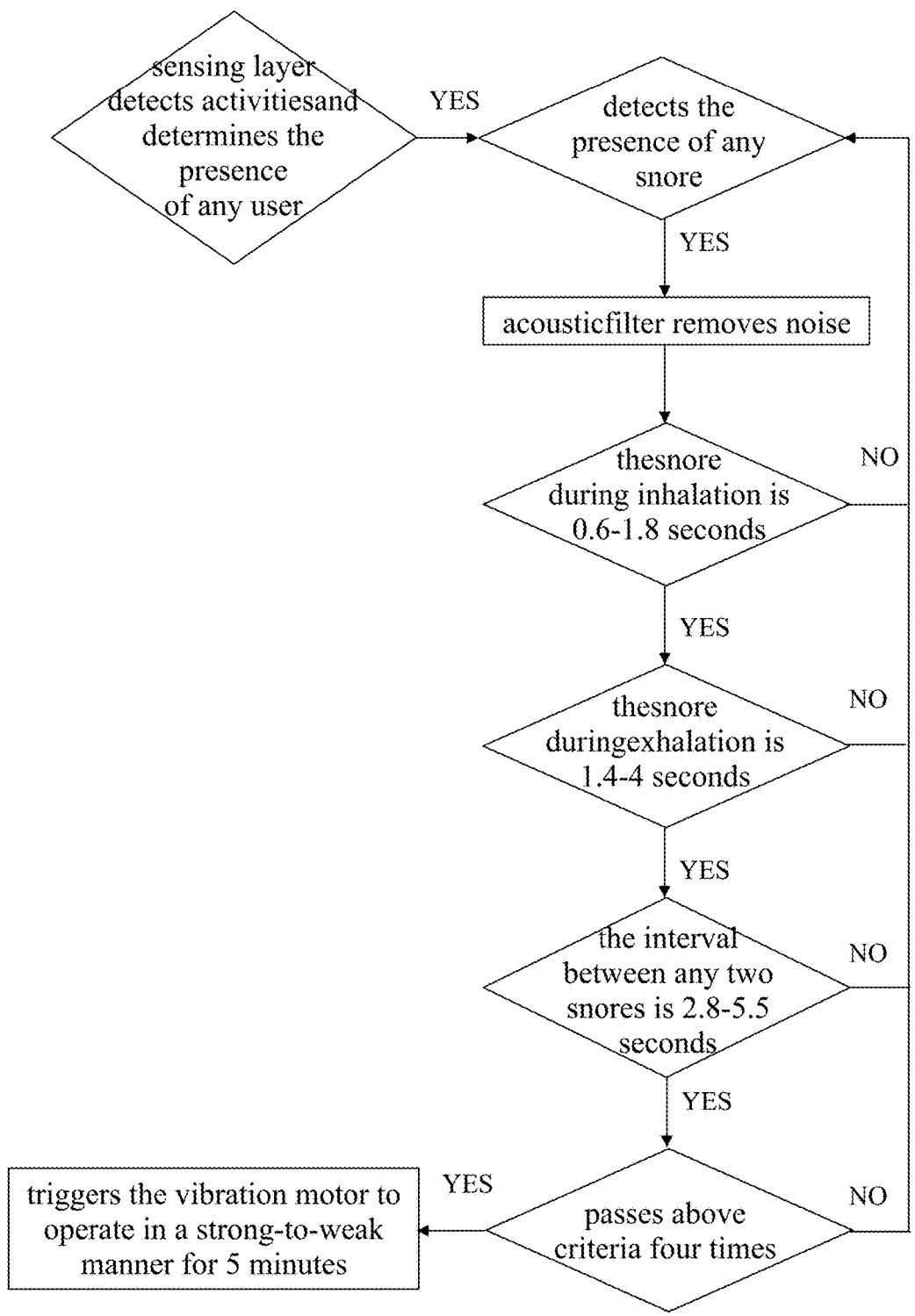
FIG. 32 is a flow chart illustrating an operating procedure of the anti-snoring mode, in accordance with some embodiments of the present invention.

Please refer to FIG. 7, FIG. 8, FIG. 27, and FIG. 32. FIG. 27 is a schematic diagram illustrating an anti-snoring mode, in accordance with some embodiments of the present invention. FIG. 32 is a flow chart illustrating an operating procedure of the anti-snoring mode, in accordance with some embodiments of the present invention. Under the anti-snoring mode 670, a user may active the anti-snoring assistance to detect any of the following events: the snoring is over 65 decibels, the duration of snoring is in a period of time, and the snoring is at a pre-determined frequency. If any of the events is detected, an anti-snoring command is generated. Once the anti-snoring command is received, the processor 41 in the controller 40 generates an anti-snoring signal to trigger at least one vibration motor 80 in the mattress or the adjustment of height of the motorized bed frame 70 to interrupt the snoring.

The operating procedure of the anti-snoring mode 670 of the application 61 is illustrated in FIG. 32. The sensing layer 20 provide at least one physiological data, such as the heart rate value, the pulse wave data, the blood pressure value, the sleep analysis data, and respiratory rate value to the controller 40. The controller 40 determines the presence of the user based on such physiological data and provides it to the anti-snoring mode 670. The smart device 60 may simultaneously detect the snoring event through the embedded microphone defined as below: a. the period of snoring is between 0.6~1.8 seconds; b. the end of the first snore and the beginning of the second snore is within 1.4-4 seconds. c. the interval between any two snores is within 2.8-5.5 seconds (i.e., the sum of the first and second conditions). d. the examination is passed if the above conditions are satisfied four times. The application 61 transmits an anti-snoring command to the controller 40 through a Bluetooth connection if the examination is passed. The controller 40 then generates an anti-snoring signal to trigger at least one vibration-based motor 80 to operate in a strong-to-weak manner for 5 minutes. If the examination fails at any of the four conditions, the examination must go over again.

Figure 14:
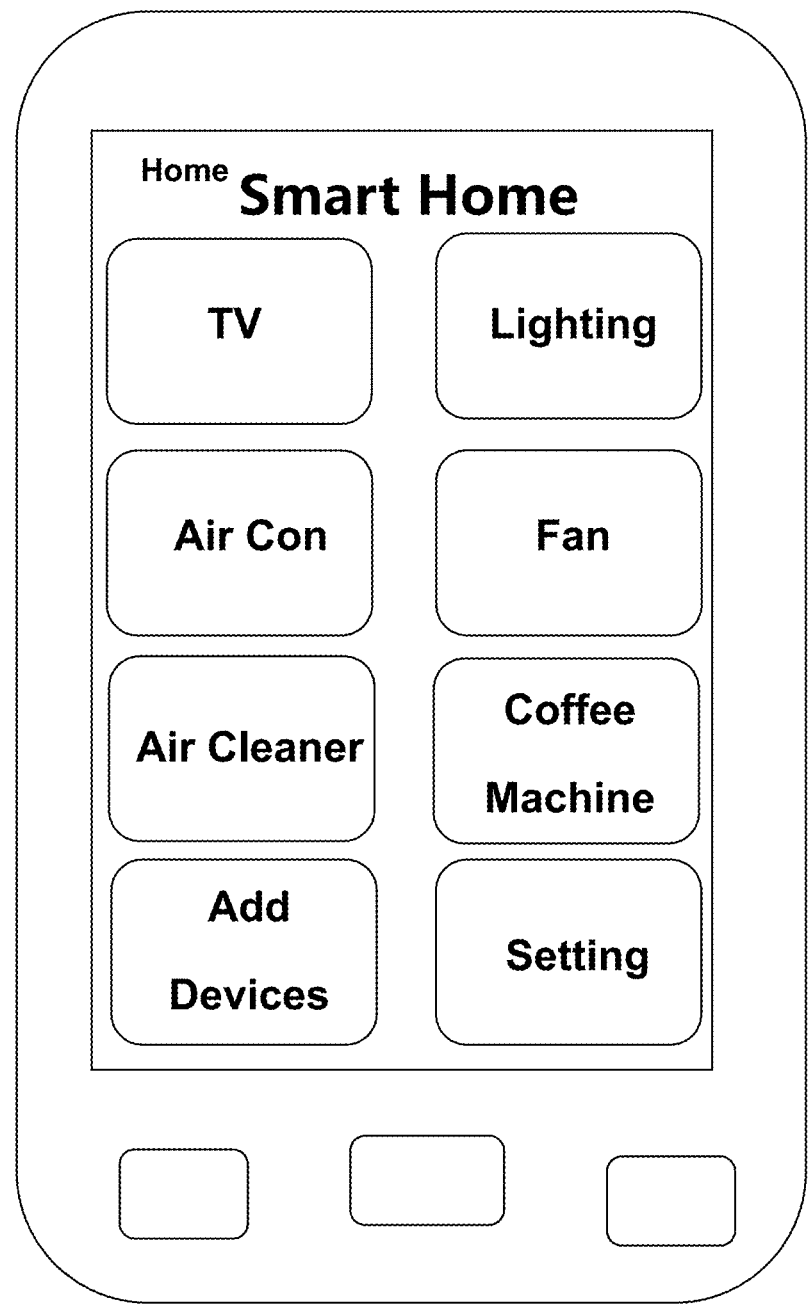
FIG. 14 is a schematic diagram illustrating a smart home mode, in accordance with some embodiments of the present invention.
Figure 24:
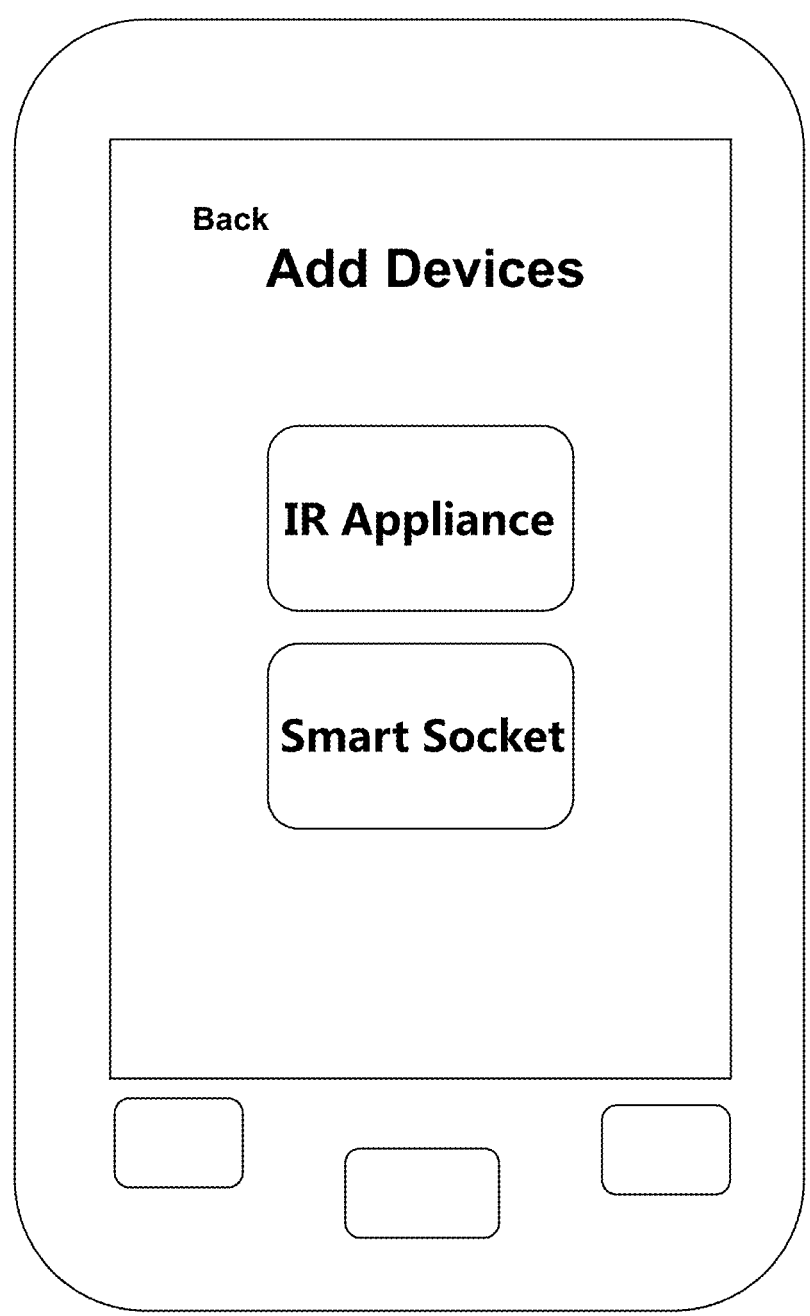
FIG. 24 is a schematic diagram illustrating the add devices page of the smart home mode, in accordance with some embodiments of the present invention.

Please refer to FIG. 7, FIG. 8, FIG. 14, and FIG. 24. FIG. 14 is a schematic diagram illustrating a smart home mode, in accordance with some embodiments of the present invention. FIG. 24 is a schematic diagram illustrating the add devices page of the smart home mode, in accordance with some embodiments of the present invention. Under the smart home mode 640, a user may select an appliance to remotely control and select a scenario to automatically control appliance, add a new appliance, and add a smart socket to generate an appliance command. Upon the receipt of the appliance command, the processor 41 in the controller 40 may generate an appliance signal to remotely control the selected appliance and automatically control the appliance based on the selected scenario, such as to regulate the temperature, humidity, and the lightness of the ambient environment of sleep. The specification of the appliance should include Bluetooth. As illustrated in FIG. 14 and FIG. 24. The smart home mode 640 may remotely control TV, lighting, air conditioner, fan, air cleaner or machine. The smart home mode 640 may also add an IR appliance or a smart socket.

The operating procedure of the smart home mode 640 of the application 61 is illustrated in FIG. 29. A user may stay on the mattress 10 and use a QR code to activate the application 61 on the smart device 60 to select the smart home mode 640. The sensing layer 20 generates physiological data based on the activities of the user and the controller 40 determines the presence of the user on the mattress 10 based on the physiological data. The controller 40 also fetch the physiological data to the application 61 through a Bluetooth 4.0 connection; the application 61 then generates a smart home command based on the physiological data and pass to the controller 40 through the Bluetooth 4.0 connection. The controller 40 generates a smart home signal based on the smart home command to control the activation of at least one vibration motor 80, a Schumann resonance generator 30, or at least one IR appliance. If the user is absent on the mattress 10, repeat step D; if the user is present on the mattress 10, moves forward to step F.

Figure 15:
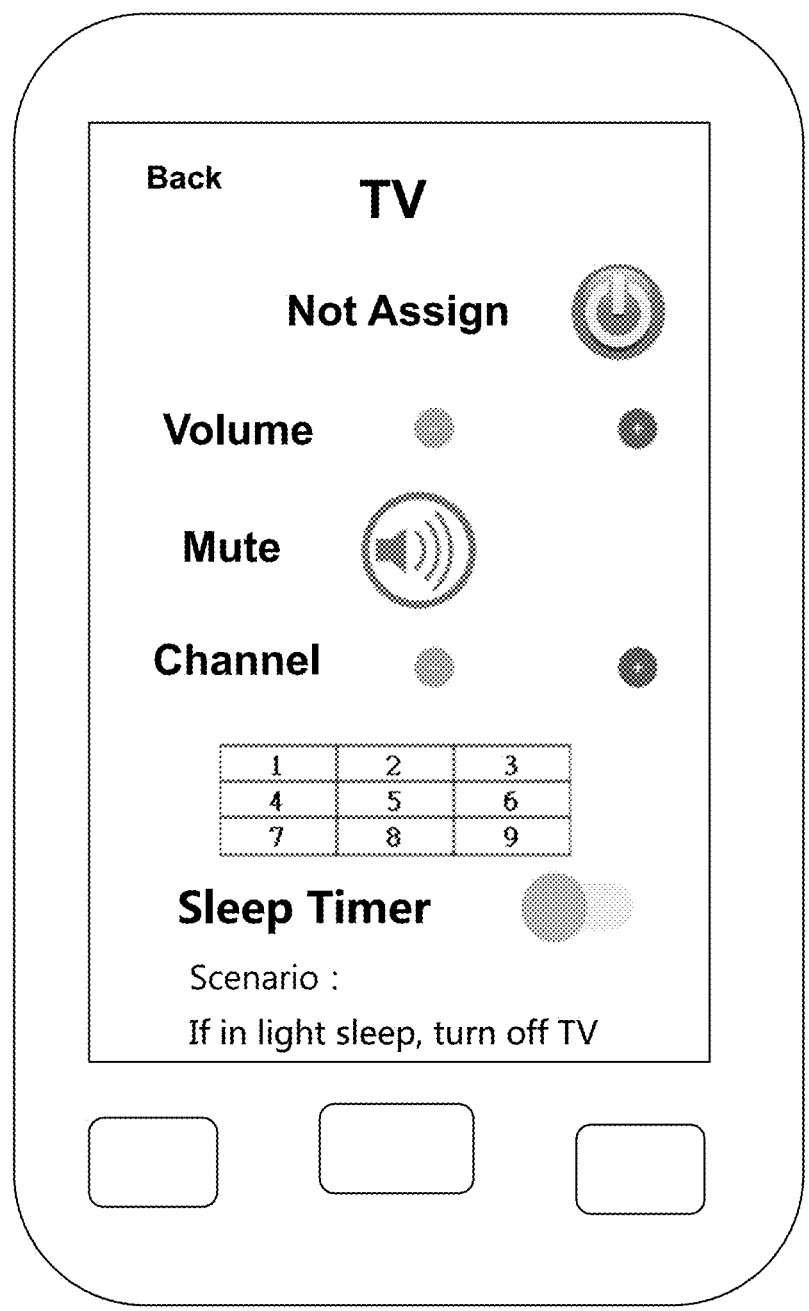
FIG. 15 is a schematic diagram illustrating a TV page of the smart home mode, in accordance with some embodiments of the present invention.
Figure 16:
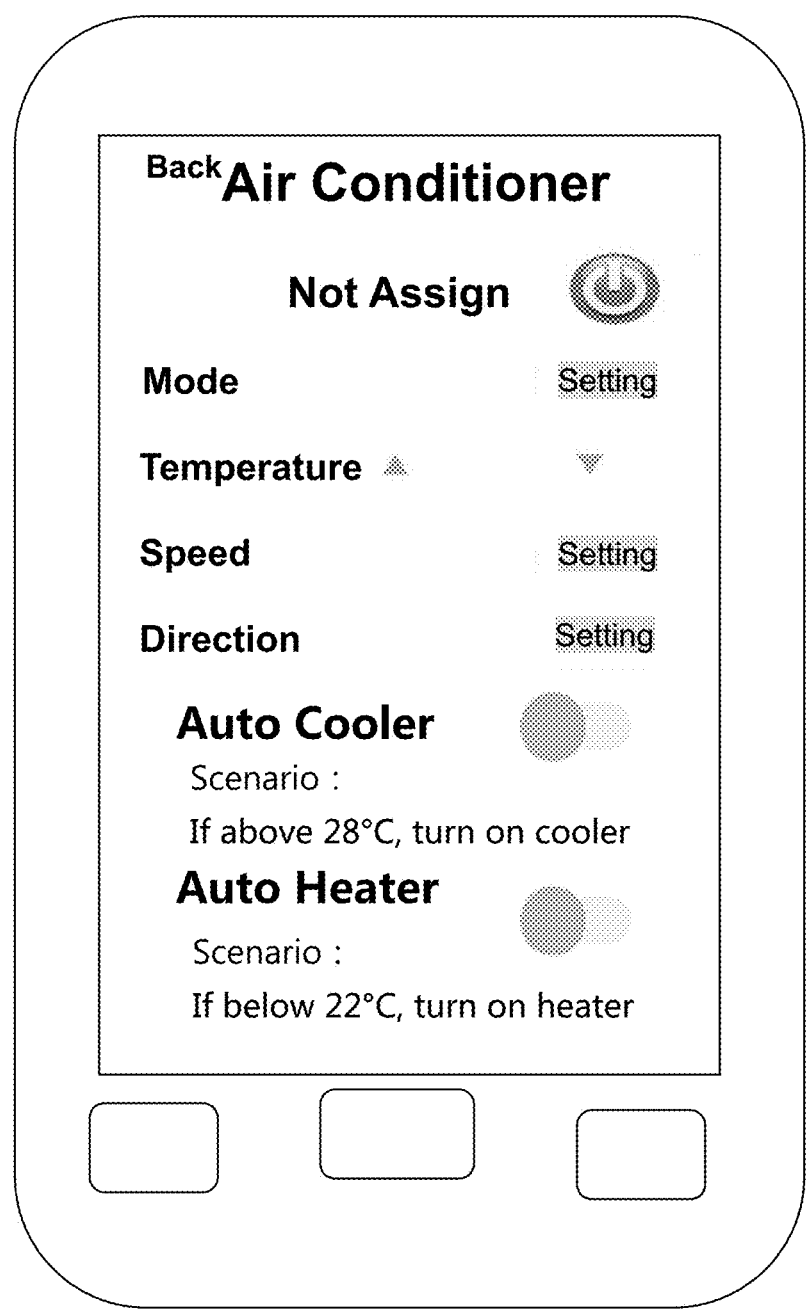
FIG. 16 is a schematic diagram illustrating an air conditioner page of the smart home mode, in accordance with some embodiments of the present invention.
Figure 17:
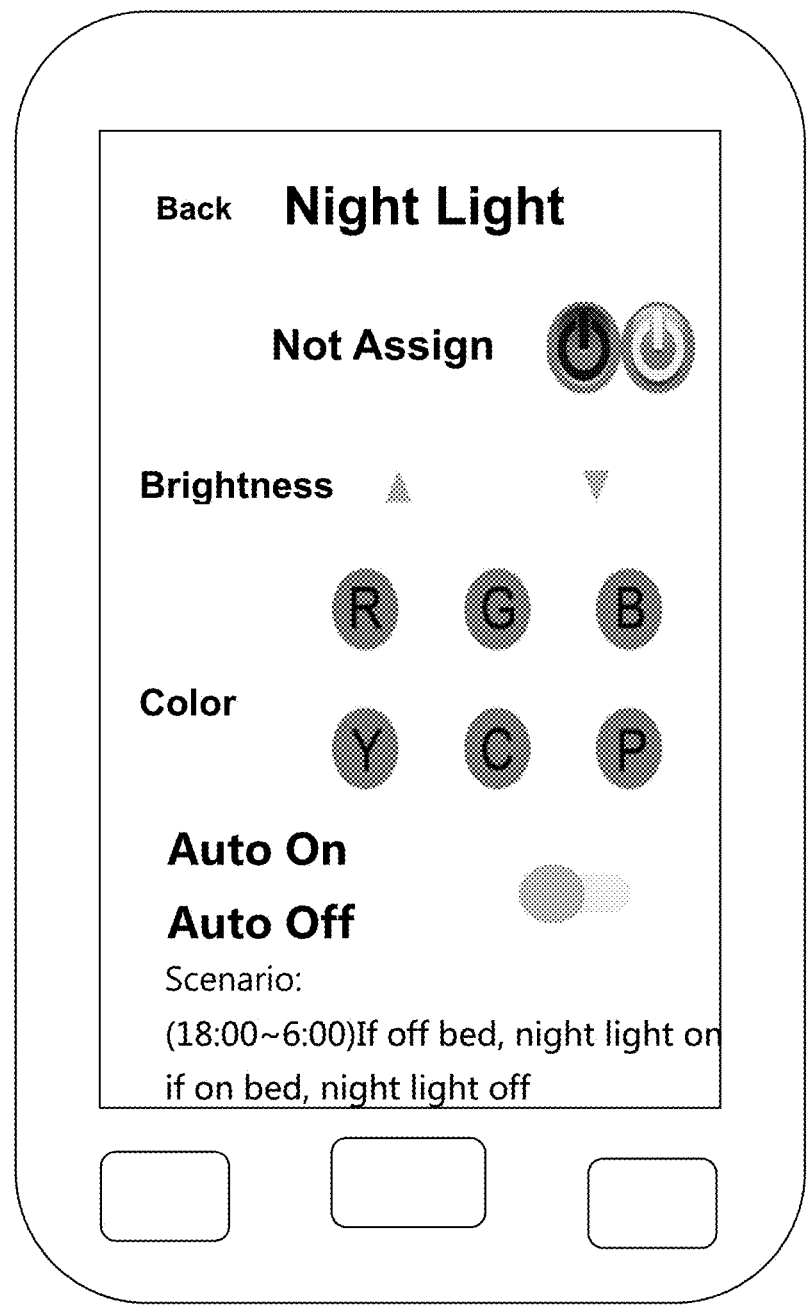
FIG. 17 is a schematic diagram illustrating a night light page of the smart home mode, in accordance with some embodiments of the present invention.
Figure 18:
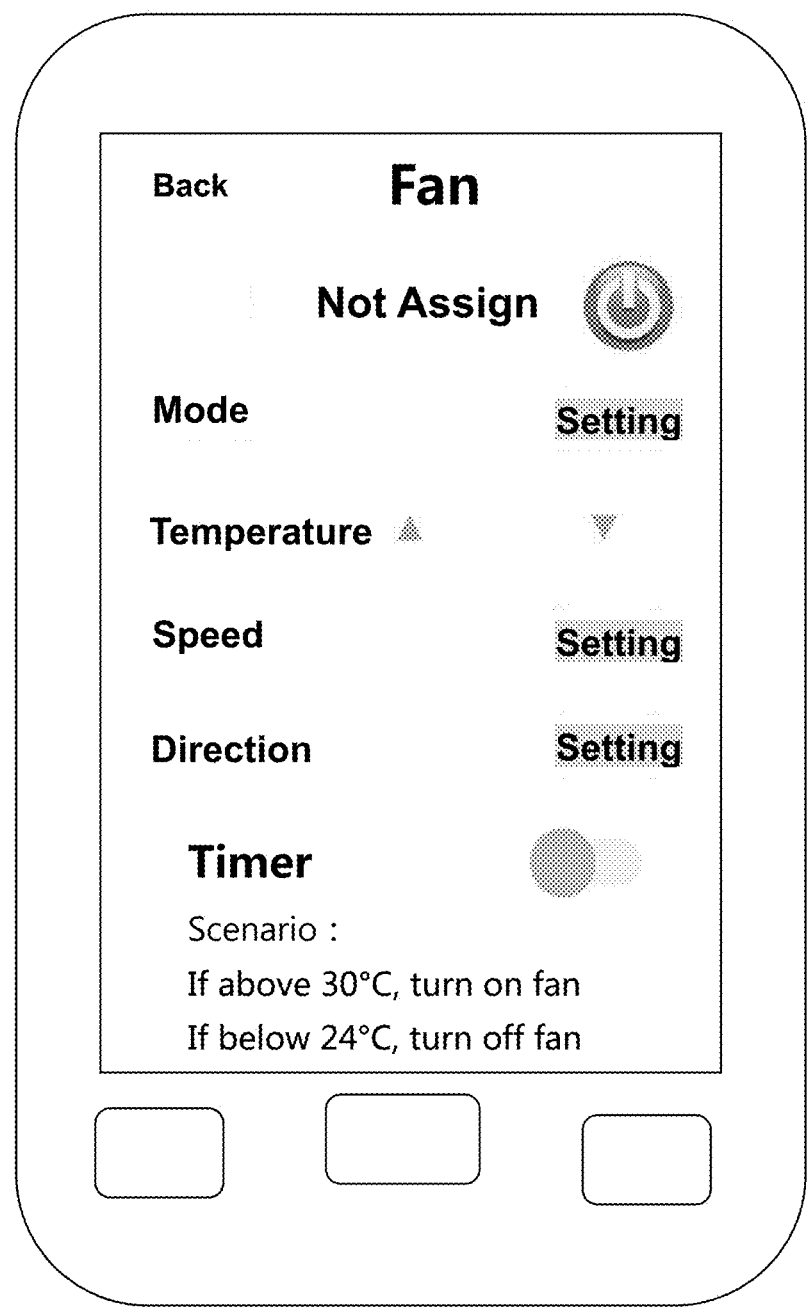
FIG. 18 is a schematic diagram illustrating a fan page of the smart home mode, in accordance with some embodiments of the present invention.
Figure 19:
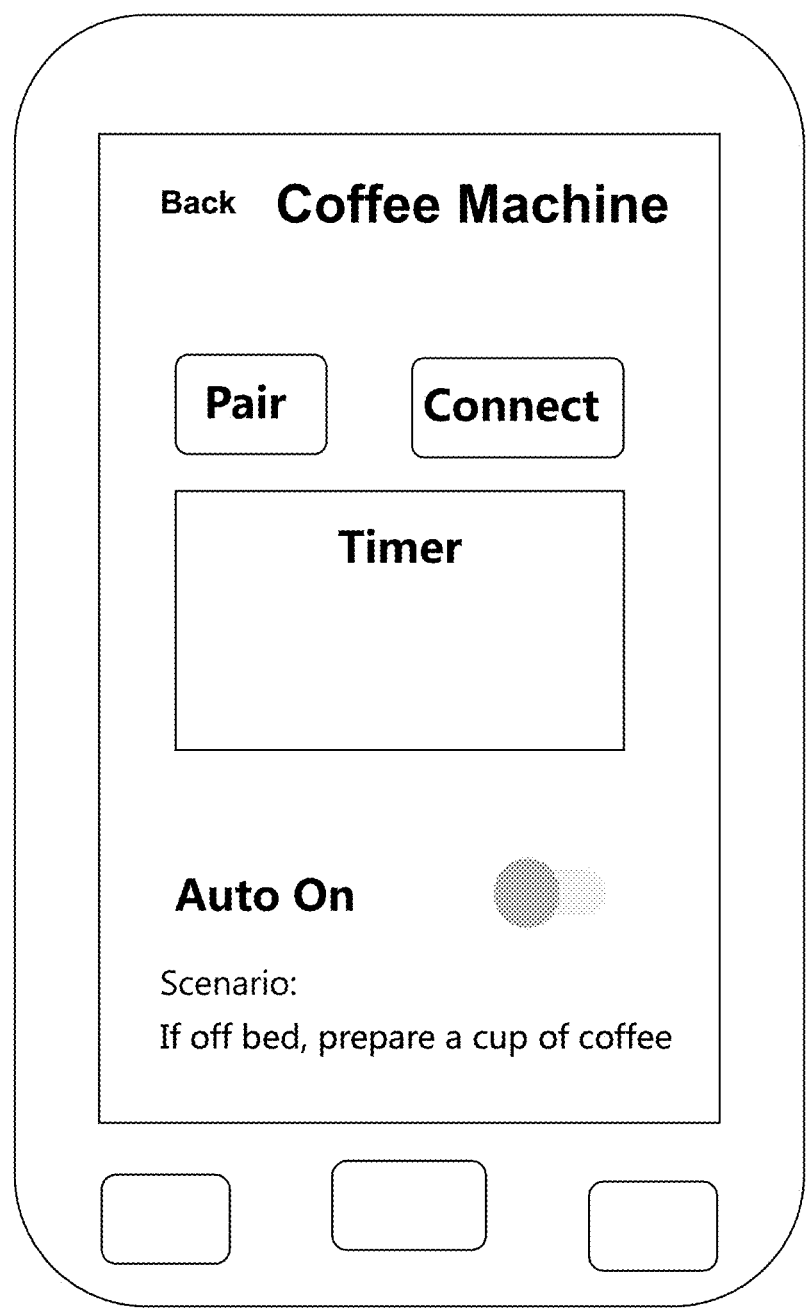
FIG. 19 is a schematic diagram illustrating a coffee machine page of the smart home mode, in accordance with some embodiments of the present invention.

Please refer to FIG. 15, FIG. 16, FIG. 17, FIG. 18, and FIG. 19. FIG. 15 is a schematic diagram illustrating a TV page of the smart home mode, in accordance with some embodiments of the present invention; FIG. 16 is a schematic diagram illustrating an air conditioner page of the smart home mode, in accordance with some embodiments of the present invention; FIG. 17 is a schematic diagram illustrating a night light page of the smart home mode, in accordance with some embodiments of the present invention; FIG. 18 is a schematic diagram illustrating a fan page of the smart home mode, in accordance with some embodiments of the present invention; and FIG. 19 is a schematic diagram illustrating a coffee machine page of the smart home mode, in accordance with some embodiments of the present invention. As illustrated in FIG. 15, a user may select the TV page to remotely control a TV and adjust volume, change channel, mute the TV, enter channel numbers, turn on and off the TV, and set a sleep timer for the TV. The power cord of the TV may connect to a Wi-Fi smart socket to enable the scenario-based controls. For example, if turns on the sleep timer and designs the scenario as that the smart socket turns off the TV when light sleep or deep sleep is detected, the TV will be automatically turned off when any of the users on the double bed falls into light sleep or deep sleep. As illustrated in FIG. 16, a user may select the air conditioner page to remotely control an air conditioner and adjust temperature, select modes, change fan speed, change air direction, turn on and off power, and timer for the air conditioner. The scenario may be set as if the temperature reaches 28° C., the air conditioner will be automatically turn on to cool down the room; if the temperature falls below 22° C., the air conditioner will be automatically turn on to heat up the room. As illustrated in FIG. 17, a user may select to remotely control a night light module and adjust lightness, change colors, turn on and off power, and turn on and off the smart night light. The scenario may be set as during 18:00 and 06:00 of the next day, the night light will be automatically turned on if the user is absent on the mattress 10 and be turned off if the user is present on the mattress 10. As illustrated in FIG. 18, a user may select the fan page to remotely control a fan and adjust temperature, select modes, change fan speed, change air direction, turn on and off power, and timer for the air conditioner. The scenario may be set as if the temperature reaches 30° C., the fan will be automatically turn on; if the temperature falls below 24° C., the fan will be automatically turn off. As illustrated in FIG. 19, the power cord of the coffee machine may be connected to a Wi-Fi smart socket to enable the scenario-based controls. A user may select the coffee machine page to remotely control a coffee machine to pair and connect a coffee machine and set the timer for the coffee machine. The scenario may be set as if the user is off from the mattress 10 during an activation time, the Wi-Fi smart socket will automatically turn on the coffee machine to brew a cup of coffee for the user. The above scenarios are for the purpose of explanation and the present invention should not be limited to such scenarios.

Figure 20:
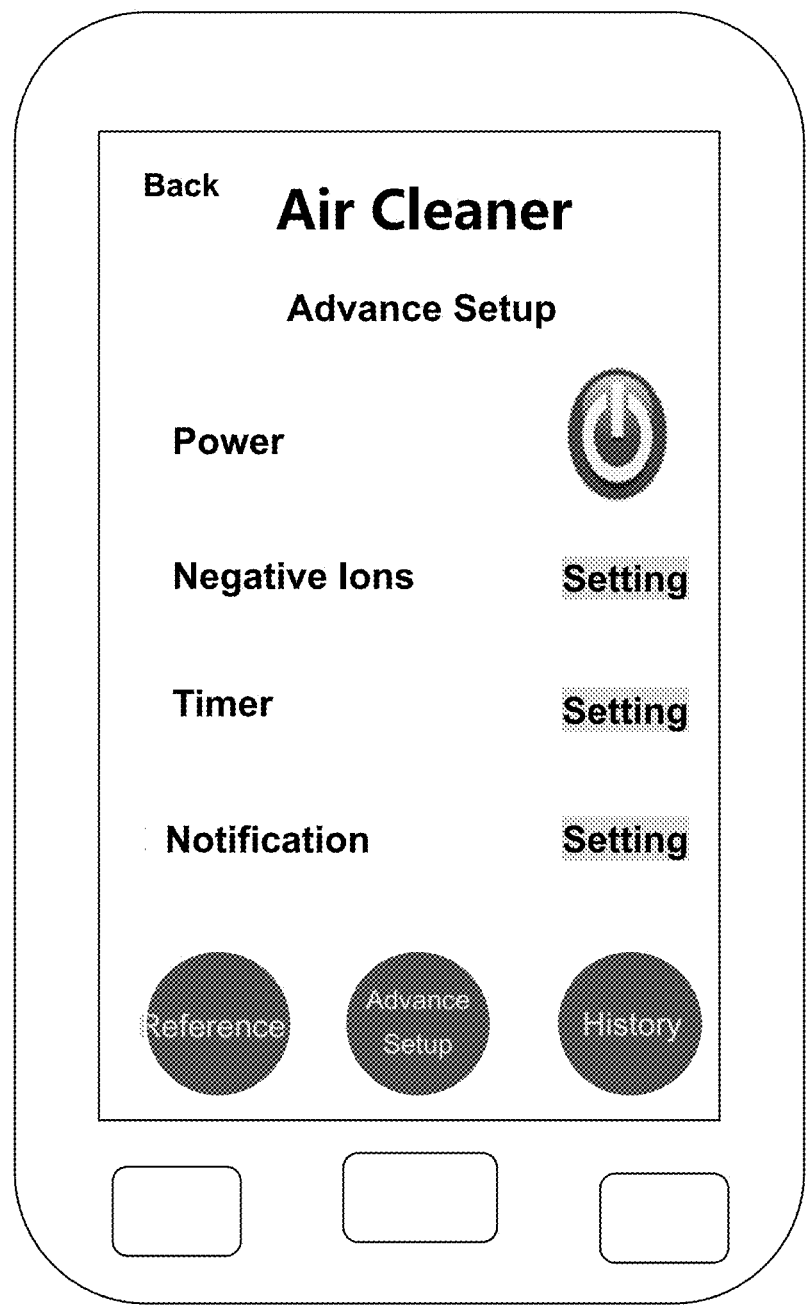
FIG. 20 is a schematic diagram illustrating an air cleaner page of the smart home mode, in accordance with some embodiments of the present invention.
Figure 21:
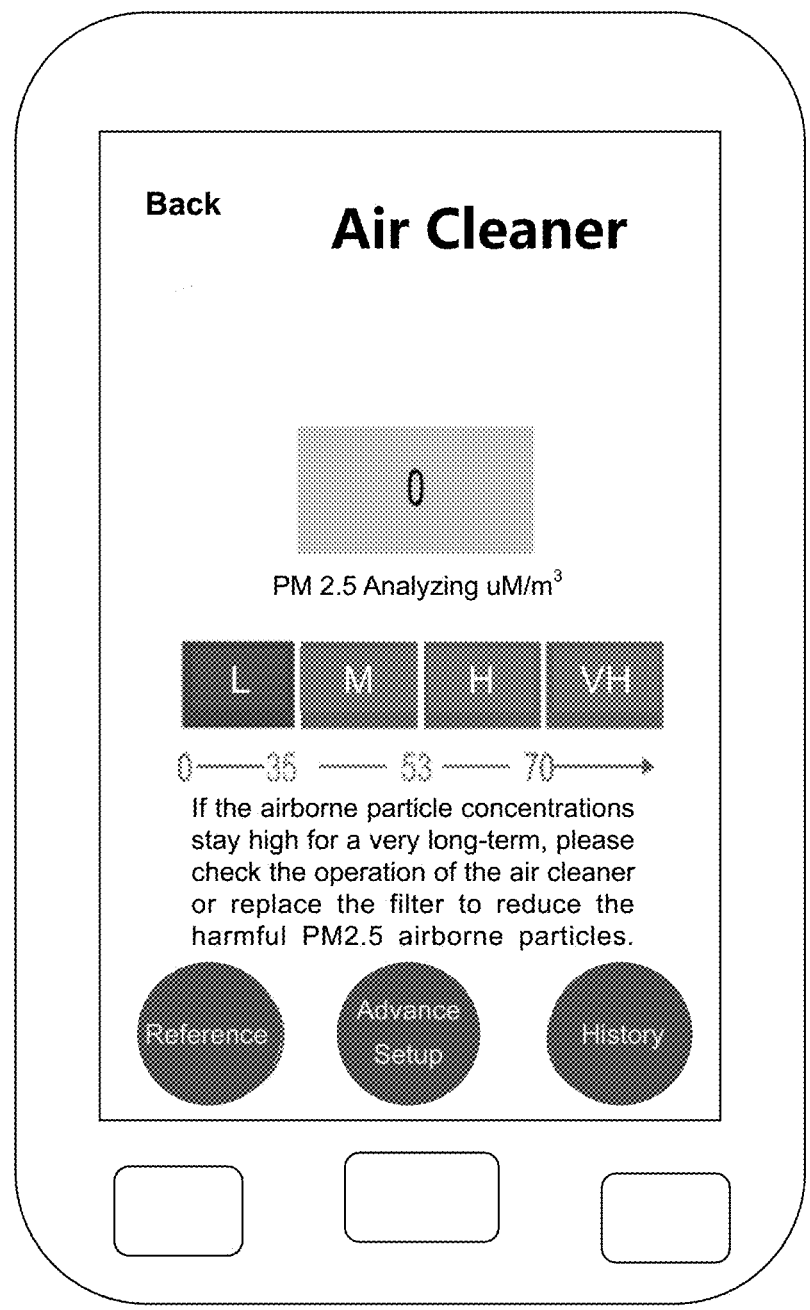
FIG. 21 is a schematic diagram illustrating another air cleaner page of the smart home mode, in accordance with some embodiments of the present invention.
Figure 22:
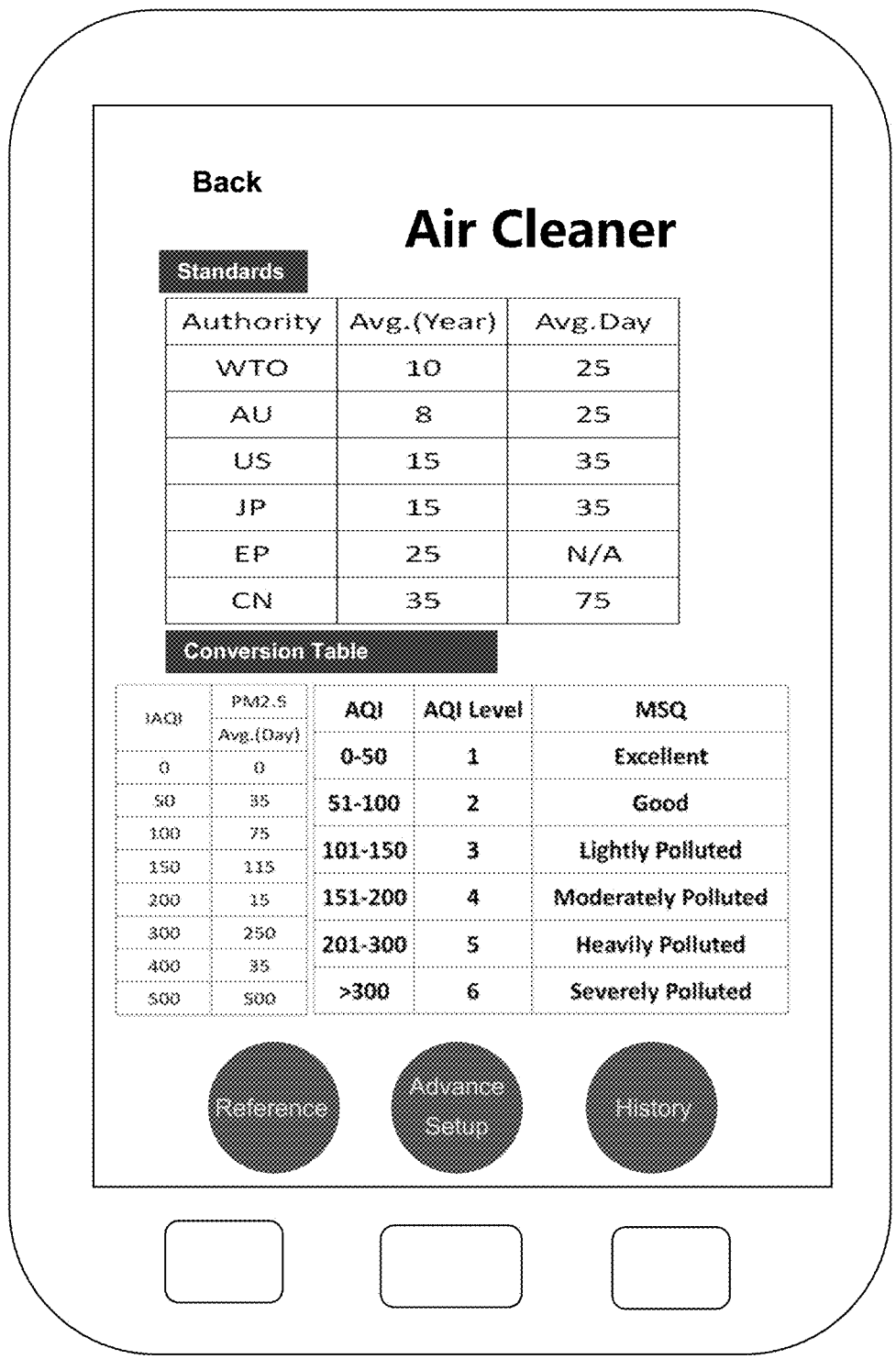
FIG. 22 is a schematic diagram illustrating yet another air cleaner page of the smart home mode, in accordance with some embodiments of the present invention.
Figure 23:
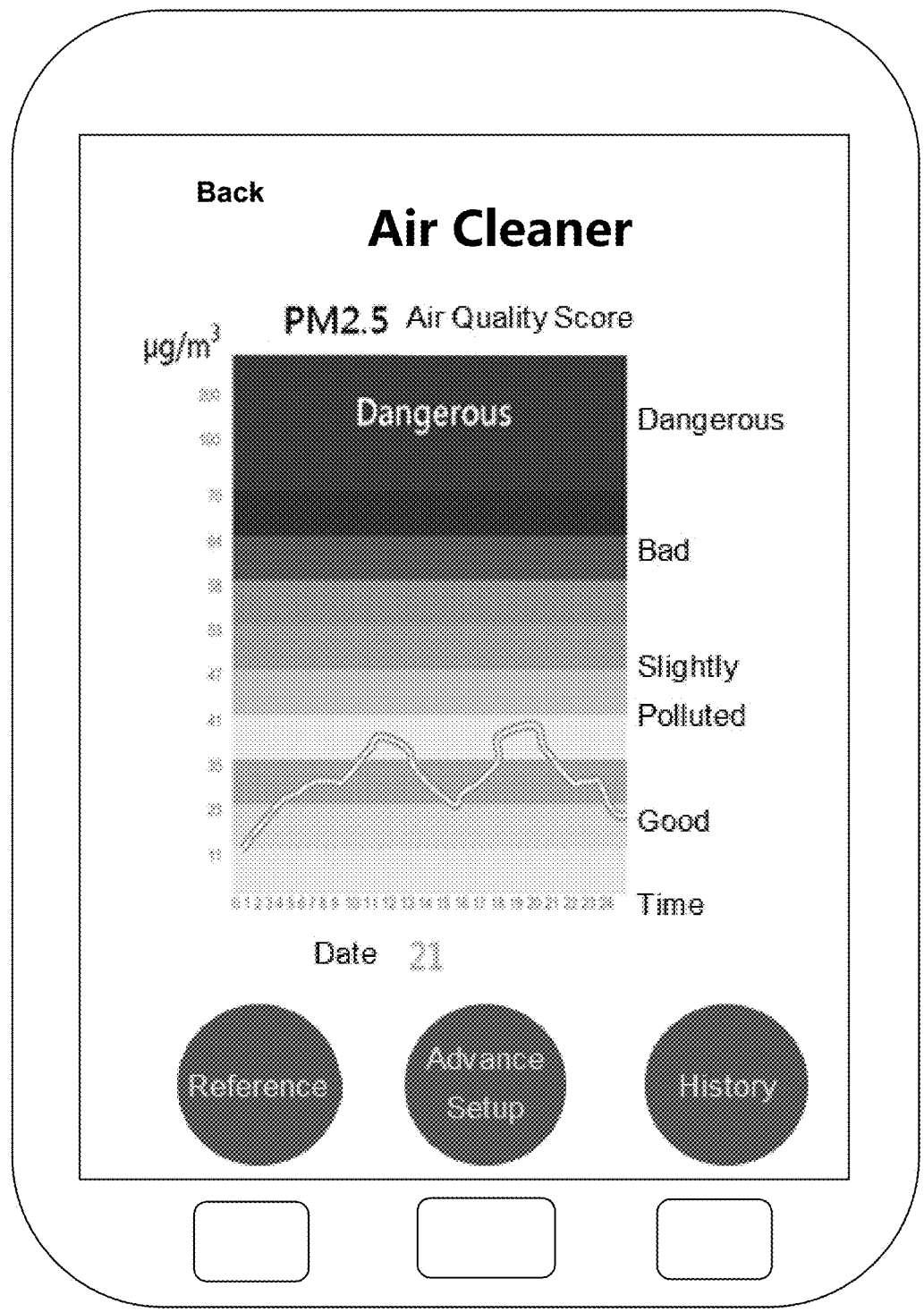
FIG. 23 is a schematic diagram illustrating yet again another air cleaner page of the smart home mode, in accordance with some embodiments of the present invention.

Please refer to FIG. 20, FIG. 21, FIG. 22, and FIG. 23. FIG. 21 is a schematic diagram illustrating another air cleaner page of the smart home mode, in accordance with some embodiments of the present invention; FIG. 22 is a schematic diagram illustrating yet another air cleaner page of the smart home mode, in accordance with some embodiments of the present invention; and FIG. 23 is a schematic diagram illustrating yet again another air cleaner page of the smart home mode, in accordance with some embodiments of the present invention. A user may select the air cleaner page to remotely control an air cleaner, analyze air quality, display references, provide advance setup, display history, and etc. As illustrated in FIG. 22, the references are a list of standards of several countries and a conversion table between IAQI and PM 2.5. As illustrated in FIG. 20 and FIG. 21, the advance setup provides the negative ions setting, the timer, and the notification of hazardous concentration, as well as the analysis of airborne particles. As illustrated in FIG. 23, the history displays the concentration of airborne particles during a day in a statistical graph.

Aside from the above appliances, other appliance such as an audio system may also be connected to the Wi-Fi smart socket and enable scenario-based controls. If turn on the sleep timer and set the scenario as that the smart socket turns off the audio system when deep sleep is detected, the audio system will be automatically turned off by the Wi-Fi smart socket when any of the users on the double bed falls into deep sleep.

Figure 33:
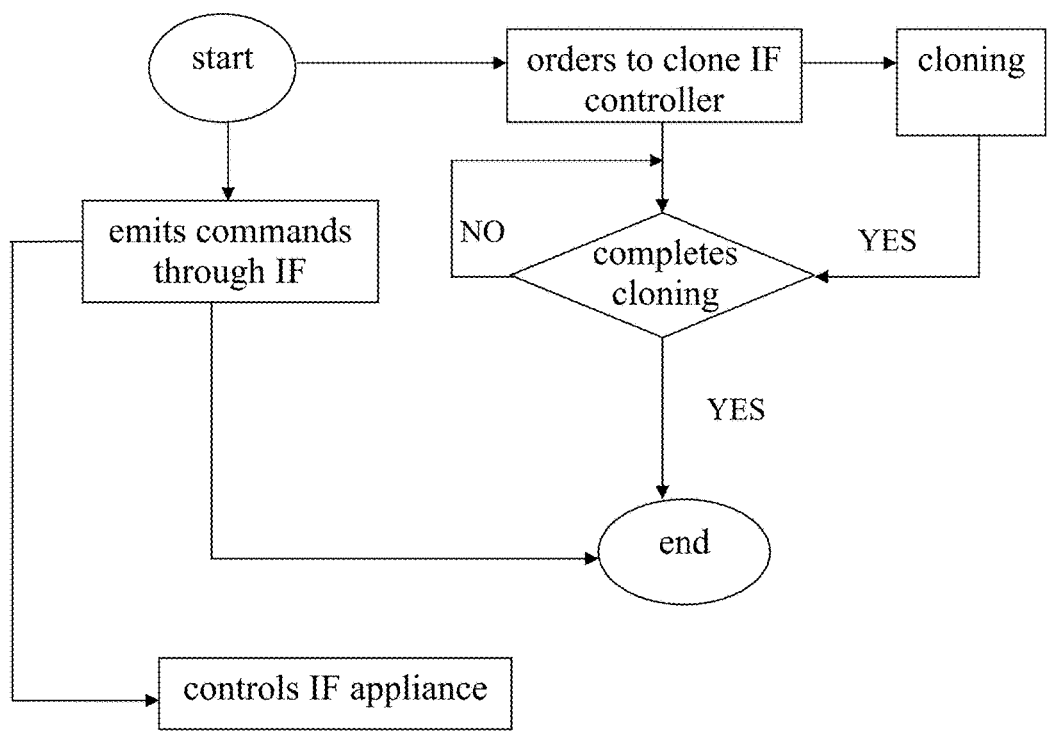
FIG. 33 is a flow chart illustrating a procedure of cloning remote controls in the smart home mode, in accordance with some embodiments of the present invention.

All the above appliance may be connected to the Wi-Fi socket and enable scenario-based controls. Please refer to FIG. 24 and FIG. 33. FIG. 33 is a flow chart illustrating a procedure of cloning IR remote controls in the smart home mode 640, in accordance with some embodiments of the present invention. In the smart home mode 640 of the application 61, the adding function may control an IR appliance through a paired universal controller after cloning the IR remote controls.

Figure 34:
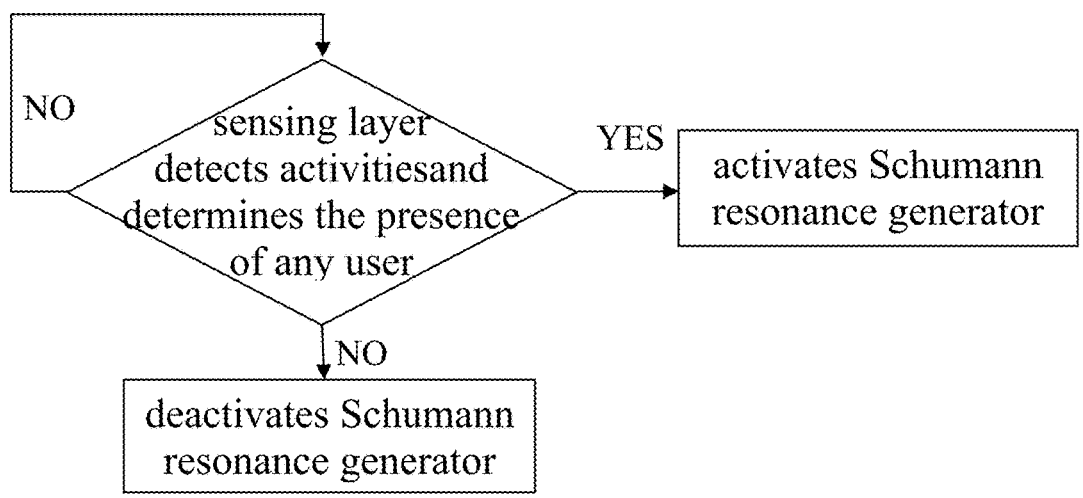
FIG. 34 is a flow chart illustrating an operating procedure of the Schumann resonance generator, in accordance with some embodiments of the present invention.

Please refer to FIG. 34. FIG. 34 is a flow chart illustrating an operating procedure of the Schumann resonance generator, in accordance with some embodiments of the present invention. The sensing layer 20 fetches at least one physiological data selected from the group consisting of a heart rate value, a pulse wave data, a blood pressure value, a respiratory rate value, and the combination thereof to the controller 40. The controller 40 then determines the presence of the user and transmits to the application 61 through a Bluetooth 4.0 connection. The application 61 then transmits an activation signal to the controller 40 through the Bluetooth 4.0 connection to activate a Schumann resonance generator 30. However, if the controller 40 detects the absence of the user, then the application 61 transmits a deactivation signal to the controller 40 to deactivate the Schumann resonance generator 30.

There are many inventions described and illustrated above. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

What is claimed is:

1. A smart bed system, comprising:
a mattress, comprising:
a sensing layer, disposed in the mattress;
a Schumann resonance generator, disposed in the mattress;
a controller disposed in the mattress, wherein the controller is electrically connected to the sensing layer and the Schumann resonance generator respectively;
a first Bluetooth transceiver, disposed in the mattress and electrically connected with the controller; and
a power supply and management system disposed in the mattress, wherein the power supply and management system is electrically connected to the controller; and
a smart device comprising:
an application configured in the smart device; and
a second Bluetooth transceiver configured in the smart device;
wherein the sensing layer is configured to generate physiological data based on the activities of a user;
wherein the application is configured to analyze the physiological data and output a command to the controller;
wherein the controller is configured to determine the presence of the user on the mattress and output a control signal based on the command;
wherein the smart device is configured to receive and display the physiological data;
wherein the control signal controls a vibration motor, the Schumann resonance generator, a motorized bed frame, or at least one infrared radiation (IR) appliance;
wherein the control signal is to trigger the vibration motor to operate in a strong-to-weak manner for 5 minutes.

2. The smart bed system as claimed in claim 1, comprises:
a motorized bed frame, disposed below the mattress; and
at least one vibration motor disposed in the mattress, wherein the at least one vibration motor is electrically connected to the controller.

3. The smart bed system as claimed in claim 1, wherein the controller comprises a processor and a memory device, wherein the processor is connected with the memory device, and wherein the processor is configured to receive and analyze the physiological data to determine the presence of the user on the mattress, wherein the processor is also configured to output the control signal based on the command, and wherein the memory device is configured to store the physiological data.

4. The smart bed system as claimed in claim 1, wherein the application comprises at least one mode selected from the group consisting of a sleep tracking mode, a sleep history mode, a bed configuration mode, a smart home mode, an alarm mode, a night light mode, and an anti-snoring mode.

5. The smart bed system as claimed in claim 4, wherein the sleep tracking mode displays heart rate values in a real-time manner or a graph depicting the history of respiratory rate.

6. The smart bed system as claimed in claim 4, wherein the sleep history mode collects one selected from the group consisting of the duration of sleep, the duration of awake time, the duration of light sleep, the duration of deep sleep, the duration on bed, the duration off bed, the ratio among awaking/light sleep/deep sleep, the frequency of tossing and turning, and the combination thereof on a daily basis, a weekly basis, or a monthly basis.

7. The smart bed system as claimed in claim 4, wherein the bed configuration mode provides options for the type of massage, the strength of massage, the linkage type of massage, and the part of massage.

8. The smart bed system as claimed in claim 4, wherein the alarm mode provides configuration to set the time of an alarm which wake the user by vibration.

9. The smart bed system as claimed in claim 4, wherein the night light mode provides configuration to set the activation time of a night light module which automatically activates the night light when the user is absent on the mattress and deactivates the night light when the user is on the mattress.

10. The smart bed system as claimed in claim 4, wherein the anti-snoring mode automatically induces vibration or adjusts the height when the snoring is over 65 decibels, the duration of snoring is in a period of time, or the snoring is at a pre-determined frequency.

11. The smart bed system as claimed in claim 1, wherein the command is a sleep tracking command, a sleep history command, a bed configuration command, a smart home command, an alarm command, a night light command, or an anti-snoring command.

12. The smart bed system as claimed in claim 1, wherein the control signal is a sleep tracking signal, a sleep history signal, a motorized bed frame signal, an appliance signal, an alarm signal, a night light signal, an anti-snoring signal.

13. The smart bed system as claimed in claim 1, wherein the physiological data comprises at least one selected from the group consist of a heart rate value, a pulse wave data, a blood pressure value, a respiratory rate value, a sleep analysis data, and the combination thereof.

14. A method of operating a smart bed system, comprising:
 providing the smart bed system as claimed in claim 1;
 providing a QR code to launch an application of a smart device;
 selecting a sleep tracking mode, a sleep history mode, a bed configuration mode, a smart home mode, an alarm mode, a night light mode, or an anti-snoring mode in the application;
 obtaining the physiological data based on the activities of the user by the sensing layer;
 determining the presence of the user based on the physiological data by the controller and sending the result to the application;
 generating the command based on the physiological data by the application to the controller; and
 generating the control signal to control a vibration motor, the Schumann resonance generator, a motorized bed frame, or at least one infrared radiation (IR) appliance;
 wherein the control signal is to trigger the vibration motor to operate in a strong-to-weak manner for 5 minutes.

15. The method as claimed in claim 14, wherein the at least one IR appliance is a TV, a fan, an air conditioner, an air cleaner, a speaker, an LED lighting, or a coffee machine.

16. The method as claimed in claim 14, wherein the anti-snoring mode detects any event selected from the group consisting of the volume of any snore is over 65 decibels, the duration of any snore is between 0.6~1.8 seconds, the duration of the end of the first snore and the beginning of the second snore is within 1.4-4 seconds, the interval between any two snores is within 2.8-5.5 seconds, and the combination thereof.

\* \* \* \* \*